(12) United States Patent
Milbrandt et al.

(10) Patent No.: US 7,776,326 B2
(45) Date of Patent: Aug. 17, 2010

(54) METHODS AND COMPOSITIONS FOR TREATING NEUROPATHIES

(75) Inventors: Jeffrey Milbrandt, St. Louis, MO (US); Toshiyuki Araki, Tokyo (JP); Yo Sasaki, Saint Louis, MO (US)

(73) Assignee: Washington University, Saint Louis, MO (US)

( * ) Notice: Subject to any disclaimer, the term of this patent is extended or adjusted under 35 U.S.C. 154(b) by 386 days.

(21) Appl. No.: 11/144,358

(22) Filed: Jun. 3, 2005

(65) Prior Publication Data

US 2006/0002914 A1 Jan. 5, 2006

Related U.S. Application Data

(60) Provisional application No. 60/577,233, filed on Jun. 4, 2004, provisional application No. 60/641,330, filed on Jan. 4, 2005.

(51) Int. Cl.
*A61K 38/00* (2006.01)

(52) U.S. Cl. .................. 424/94.5; 435/183; 435/366

(58) Field of Classification Search ............ 424/94.5
See application file for complete search history.

(56) References Cited

U.S. PATENT DOCUMENTS

| | | | |
|---|---|---|---|
| 6,573,299 B1 | 6/2003 | Petrus | |
| 7,345,178 B2 * | 3/2008 | Nunes et al. | 548/154 |
| 7,544,497 B2 * | 6/2009 | Sinclair et al. | 435/183 |
| 2002/0106354 A1 | 8/2002 | Anderson et al. | |
| 2002/0182196 A1 | 12/2002 | McCleary | |
| 2003/0045498 A1 | 3/2003 | Kovesdi et al. | |
| 2003/0162277 A1 | 8/2003 | Bird et al. | |
| 2005/0080024 A1 * | 4/2005 | Tucker et al. | 514/27 |
| 2005/0096256 A1 * | 5/2005 | Sinclair | 514/2 |
| 2005/0227327 A1 * | 10/2005 | Brenner | 435/69.1 |
| 2006/0025337 A1 * | 2/2006 | Sinclair et al. | 514/12 |
| 2007/0027095 A1 * | 2/2007 | Brenner | 514/43 |
| 2007/0105109 A1 * | 5/2007 | Geesaman et al. | 435/6 |

FOREIGN PATENT DOCUMENTS

| | | |
|---|---|---|
| CN | 1270034 A | 10/2000 |
| FR | 2842424 | 1/2004 |
| WO | WO2004/016726 * | 2/2004 |
| WO | WO 2005/002672 A2 | 1/2005 |

OTHER PUBLICATIONS

Keswani et al., Chapter 11—"An Endogenous Pathway Preventing Axonal Degeneration Mediated by Schwann Cell-Derived Erythropoietin" in Erythropoietin and the Nervous System, Novel Therapeutic Options for Neuroprotection, 2006, Springer US, Ahmet Höke, Ed.*
Araki et al., "Increased Nuclear NAD Biosynthesis and SIRT1 activation Prevent Axonal Degeneration," Science, 2004, pp. 1010-1013.
Samsam et al., "The $Wld^S$ Mutation Delays Robust Loss of Motor and Sensory Axons in a Genetic Model for Myelin-Related Axonopathy," J. Neurosci, 2003, pp. 2833-2839, vol. 23.
Anderson et al., "Manipulation of a Nuclear $NAD^+$ Salvage Pathway Delays Aging Without Altering Steady-State $NAD^+$ Levels," J. Biol. Chem., 2002, pp. 18881-18890, vol. 277.
Anderson et al., "Yeast Life-Span Extension by Calorie Restriction is Independent of NAD Fluctuation," Science, 2003, pp. 2124-2126, vol. 302.
Bastianetto et al., "Neuroprotective Abilities of Resveratrol and Other Red Wine Constituents Against Nitric Oxide-Related Toxicity in Cultured Hippocampal Neurons," Brit. J. Pharmacol., 2000, pp. 711-720, vol. 131.
Bieganowski et al., "Discoveries of Nicotinamide Riboside as a Nutrient and Conserved *NRK* Genes Establish a Preiss-Handler Independent Route to $NAD^+$ in Fungi and Humans," Cell, 2004, pp. 495-502, vol. 117.
Bitterman et al., "Longevity Regulation in *Saccharomyces cerevisiae*: Linking Metabolism, Genome Stability, and heterochromatin," Microbiol. Mol. Biol. Rev., 2003, pp. 376-399, vol. 67.
Brunet et al., "Stress-Dependent Regulation of FOXO Transcription Factors by the SIRT1 Deacetylase," Sciencexpress, 2004, 10 pages.
Bruzzone et al., "Connexin 43 Hemi Channels Mediate$^{Ca2+}$ -regulated Transmembrane $NAD^+$ Fluxes in Intact Cells," Faseb. J., 2001, pp. 10-12, vol. 15.

(Continued)

*Primary Examiner*—Herbert J. Lilling
(74) *Attorney, Agent, or Firm*—Zackson Law LLC.

(57) ABSTRACT

Methods of treating or preventing axonal degradation in neuropathic diseases in mammals are disclosed. The methods can comprise administering to the mammal an effective amount of an agent that acts by increasing sirtuin activity in diseased and/or injured neurons. The methods can also comprise administering to the mammal an effective amount of an agent that acts by increasing NAD activity in diseased and/or injured neurons. Also disclosed are methods of screening agents for treating a neuropathies and recombinant vectors for treating or preventing neuropathies.

6 Claims, 8 Drawing Sheets

OTHER PUBLICATIONS

Buck et al., "Diversity in the Sir2 Family of Protein Deacetylases," J. Leukoc. Biol., 2004, pp. 939-950, vol. 75.

Buckmaster et al., "The Rate of Wallerian Degeneration in Cultured Neurons from Wild Type and C57BL/Wld$^S$ Mice Depends on Time in Culture and May be Extended in the Presence of Elevated K$^+$ Levels," Eur. J. Neurosci., 1995, pp. 1596-1602, vol. 7.

Castanotto et al., "Functional siRNA Expression from Transfected PCR Products," RNA, 2002, pp. 1454-1460, vol. 8.

Coleman et al., "Axon Pathology in Neurological Disease: A Neglected Therapeutic Target," Trends Neurosci., 2002, pp. 532-537, vol. 25.

Ferguson, "Role of Plant Polyphenols in Genomic Stability," Mutation Res., 2001, pp. 89-111, vol. 475.

Ferri et al., "Inhibiting Axon Degeneration and Synapse Loss Attenuates Apoptosis and Disease Progression in a Mouse Model of Motorneuron Disease," Current Biol., 2003, pp. 669-673, vol. 13.

Gillingwater et al., "Neuroprotection After Transient Global Cerebral Ischemia in Wld$^S$ Mutant Mice," J. Cereb. Blood Flow Metab., 2004, pp. 62-66, vol. 24.

Gillingwater et al., "Age-Dependent Synapse Withdrawal at Axotomised Neuromuscular Junctions in Wld$^S$ Mutant and Ube4b/Nmnat Transgenic Mice," J. Physiol., 2002, pp. 739-755, vol. 543.

Gillingwater et al., "Compartmental Neurodegeneration and Synaptic plasticity in the Wld Mutant$^S$ Mouse," J. Physiol., 2001, p. 627-639, vol. 534.

Grozinger et al., "Indentification of a Class of Small Molecule Inhibitors of the Sirtuin Family of NAD-Dependent Deacetylases by Phenotype Screening," J. Biol. Chem., 2001, pp. 38837-38843, vol. 276.

Hekimi et al., Genetics and the Specificity of the Aging Process, Science, 2003, pp. 1351-1354, vol. 299.

Howitz et al., "Small Molecule Activators of Sirtuins Extend *Saccharomyces cerevisiae* Lifespan," Nature, 2003, pp. 191-196, vol. 425.

Huh et al., "Global Analysis of Protein Localization in Budding Yeast," Nature, 2003, pp. 686-691, vol. 425.

Jang et al., "Cancer Chemopreventive Activity of Resveratrol, a Natural Product Derived from Grapes," Science, 1997, pp. 218-220, vol. 275.

Lassmann et al., "Ultrastructural Sequence of Myelin Degradation. Wallerian Degeneration in the Rat Optic Nerve," Acta. Neuropathol., 1978, pp. 91-102, vol. 44.

Lin et al., "Nicotinamide Adenine Dinucleotide, a Metabolic Regulator of Transcription, Longevity and Disease," Current Opin. Cell Biol., 2003, pp. 241-246, vol. 15.

Lin et al., "Requirement of NAD and *SIR2* for Life-Span Extension by Calorie Restriction in *Saccharomyces cerevisiae*," Science, 2000, pp. 2126-2128, vol. 289.

Lois et al., "Germline Transmission and Tissue-Specific Expression of Transgenes Delivered by Lentiviral Vectors," Science, 2002, pp. 868-872, vol. 295.

Mack et al., "Wallerian Degeneration of Injured Axons an Dynapses is Delayed by a *Ube4b/Nmnat* Chimeric Gene," Nat. Neurosci., 2001, pp. 1199-1206, vol. 4.

Magni et al., "Enzymology of NAD$^+$ Homeostasis in Man," Cell Mol. Life Sci., 2004, pp. 19-34, vol. 61.

Middleton, Jr., "The Effects of Plant Flavonoids on Mammalian Cells: Implications for Inflammation, Heart Disease, and Cancer," Pharmacol. Rev., 2000, pp. 673-751, vol. 52.

Nicolini et al., "Anti-Apoptotic Effects of *Trans*-Reveratrol on Paclitaxel-Induced Apoptosis in the Human Neuroblastoma SH-SY5Y Cell Line," Neurosci. Lett., 2001, pp. 41-44, vol. 302.

Pan et al., "Effects of Neurotoxic and Neuroprotective Agents on Peripheral Nerve Regeneration Assayed by Time-Lapse Imaging In Vivo," J. Neurosci., 2003, pp. 11479-11488, vol. 23.

Raff et al., "Axonal Self-Destruction and Neurodegeneration," Science, 2002, pp. 868-871, vol. 296.

Sajadi et al., "Wld$^S$-Mediated Protection of Dopaminergic Fibers in an Animal model of Parkinson Disease," Current Biol., 2004, pp. 326-330, vol. 14.

Savaskan et al., "Red Wine Ingredient Resveratrol Protects from β-Amyloid Neurotoxicity," Gerontol., 2002, pp. 380-383, vol. 49.

Schmalbruch et al., "A New Mouse Mutant with Progressive Motor Neuronopathy," J. Neuropathol. Exp. Neurol., 1991, pp. 192-204, vol. 50.

Skaper, "Poly(ADP-Ribose) Polymerase-1 in Acute Neuronal Death and Inflammation," Ann. NY Acad. Sci., 2003, pp. 217-228, vol. 993.

Skaper, "Questions and Answers, Session VI: Mechanisms of Neuroprotection," Ann. NY Acad. Sci., 2003, pp. 287-288, vol. 993.

Smith, "Human Sir2 and the 'Silencing' of p53 Activity," Trends Cell Biol., 2002, pp. 404-406, vol. 12.

Szabo et al. "DNA Strand Breakage, Activation of Poly(ADP-Robose) Synthetase, and Cellular Energy Depletion Are Involved in the Cytotoxicity in Macrophages and Smooth Muscle Cells Exposed to Peroxynitrite," Proc. Natl. Acad. Sci. USA, 1996, pp. 1753-1758, vol. 93.

Virgili et al., "Partial Neuroprotection of in Vivo Excitotoxic Brain Damage by Chronic Administration of the Red Wine Antioxidant Agent, Trans-Resveratrol in Rats," Neurosci. Lett., 2000, pp. 123-126, vol. 281.

Waller, "Experiments on the Section of the Glossopharyngeal and Hypoglossal Nerves of the Frog, and Observations of the Alterations Produced Thereby in the Structure of Their Primitive Fibres," Philos. Trans. R. Soc. Lond., 1850, pp. 423-429, vol. 140.

Wang et al., "*Wld$^S$* Mice are Resistant to Paclitaxel (Taxol) Neuropathy," Ann. Neurol., 2002, pp. 442-447, vol. 52.

Zhai et al., "Involvement of the Ubiquitin-Proteasome System in the Early Stages of Wallerian Degeneration," Neuron, 2003, pp. 217-225, vol. 39.

Chinese-language Office Action in related application No. 200580018114.8 dated Apr. 25, 2008.

English-language translation of Chinese-language Office Action in related application No. 200500018114.8 dated Apr. 25, 2008 "Chinese Office Action and translation of CN1270034A".

English-language translation of Chinese-language Office Action in related application No. 200500018114.8 dated Apr. 25, 2008 "Notice of Opinion of First Examination".

International Search Report issued on Aug. 6, 2008 in connection with corresponding PCT Application No. PCT/US08/01085.

Supplemental ESR and Written Opinion, issued Feb. 4, 2010 in the related application EP 05 79 0283.

Ferri et al., The neuroprotective protein Wld(s) can delay neurodegeneration in a mouse model with motor neuron disease, Abstracts of the Annual Meeting of the Society for Neuroscience, Nov. 2002, vol. 32, 1, Society for Neuroscience, Washington DC [Abstract].

Frye, Phylogenetic classification of prokaryotic and eukaryotic Sir2-like proteins, Biochem. Biophys. Res. Comm., 2000, p. 793-798, vol. 273, No. 2.

Garavaglia et al., Structure of human NMN adenylyltransferase: A key nuclear enzyme for NAD homeostasis, J. Biol. Chem., 2002, p. 8524-8530, vol. 277, No. 10.

Wang et al., The Wld(s) protein protects against axonal degeneration: A model of gene therapy for peripheral neuropathy, Ann. Neurol., 2001, p. 773-779, vol. 50, No. 6.

* cited by examiner

METHODS AND COMPOSITIONS FOR TREATING NEUROPATHIES

RELATED APPLICATION DATA

This application claims benefit under 35 U.S.C. §119(e) to U.S. Provisional Application Ser. No. 60/577,233, filed Jun. 4, 2004 and U.S. Provisional Application Ser. No. 60/641,330, filed Jan. 4, 2005. These applications are incorporated herein in their entireties by reference.

GOVERNMENT INTERESTS

This work was supported at least in part with funds from the federal government under U.S.P.H.S. 5RO1 NS40745. The U.S. Government may have certain rights in the invention.

FIELD

This invention relates generally to diseases and conditions involving neurons and, more particularly, to methods and compositions for treating or preventing neuropathies and other diseases and conditions involving neurodegeneration. Also included are methods of identifying agents for treating or preventing neuropathies.

BACKGROUND

Axon degeneration occurs in a variety of neurodegenerative diseases such as Parkinson's and Alzheimer's diseases as well as upon traumatic, toxic or ischemic injury to neurons. Such diseases and conditions are associated with axonopathies including axonal dysfunction. One example of axonopathy is Wallerian degeneration (Waller, Philos Trans R. soc. Lond. 140:423-429, 1850), which occurs when the distal portion of the axon is severed from the cell body. The severed axon rapidly succumbs to degeneration. Axonopathy can, therefore, be a critical feature of neuropathic diseases and conditions and axonal deficits can be an important component of the patient's disability.

SUMMARY

Accordingly, the present inventors have succeeded in discovering that axonal degeneration can be diminished or prevented by increasing NAD activity in diseased and/or injured neurons. It is believed that the increased NAD activity can act to increase sirtuin activity which then produces a decrease in axonal degeneration of injured neuronal cells. Thus, one approach to preventing axonal degeneration can be by activating sirtuin molecules, i.e. SIRT1 in injured mammalian axons. The activation of SIRT1 can be through direct action on the SIRT1 molecule or by increasing the supply of nicotinamide adenine dinucleotide (NAD) which acts as a substrate for the histone/protein deacetylase activity of SIRT1. The activation of SIRT1 results in a decrease in severity of axonal degeneration or a prevention of axonal degeneration. It is also believed possible that the increase in NAD activity could act through other mechanisms not involving sirtuin. Thus, increasing NAD activity, which may act through increasing SIRT1 activity or through one or more other mechanisms or both can diminish or prevent axonal degeneration in injured mammalian axons.

Thus, in various embodiments, the present invention is directed to a method of treating or preventing a neuropathy in a mammal and, in particular, in a human in need thereof. The method can comprise administering an effective amount of an agent that acts to increase sirtuin activity and, in particular, SIRT1 activity in diseased and/or injured neurons.

In various embodiments, the agent can increase SIRT1 activity through increasing NAD activity. It is believed that increasing NAD activity can increase sirtuin activity because NAD can act as a substrate of SIRT1. Such agents can include NAD or NADH, a precursor of NAD, an intermediate in the NAD salvage pathway or a substance that generates NAD such as a nicotinamide mononucleotide adenylyltransferase (NMNAT) or a nucleic acid encoding a nicotinamide mononucleotide adenylyltransferase. The nicotinamide mononucleotide adenylyltransferase can be an NMNAT1 protein.

In various embodiments, the agent can also act to directly increase SIRT1 activity and as such, the agent can be a sirtuin polypeptide or a nucleic acid encoding a sirtuin polypeptide or a substance such as a stilbene, a chalcone, a flavone, an isoflavanone, a flavanone or a catechin. Such compounds can include a stilbene selected from the group consisting of resveratrol, piceatannol, deoxyrhapontin, trans-stilbene and rhapontin; a chalcone selected from the group consisting of butein, isoliquiritigen and 3,4,2',4',6'-pentahydroxychalcone; a flavone selected from the group consisting of fisetin, 5,7,3',4',5'-pentahydroxyflavone, luteolin, 3,6,3',4'-tetrahydroxyflavone, quercetin, 7,3',4',5'-tetrahydroxyflavone, kaempferol, 6-hydroxyapigenin, apigenin, 3,6,2',4'-tetrahydroxyflavone, 7,4'-dihydroxyflavone, 7,8,3',4'-tetrahydroxyflavone, 3,6,2',3'-tetrahydroxyflavone, 4'-hydroxyflavone, 5,4'-dihydroxyflavone, 5,7-dihydroxyflavone, morin, flavone and 5-hydroxyflavone; an isoflavone selected from the group consisting of daidzein and genistein; a flavanone selected from the group consisting of naringenin, 3,5,7,3',4'-pentahydroxyflavanone, and flavanone or a catechin selected from the group consisting of (−)-epicatechin, (−)-catechin, (−)-gallocatechin, (+)-catechin and (+)-epicatechin.

In various embodiments, the invention can also involve methods of treating a neuropathy by administering to a mammal and, in particular, a human, an effective amount of an agent that acts by increasing nuclear NAD activity in diseased and/or injured neurons and/or supporting cells such as, for example, glia, muscle cells, fibroblasts, etc.

Such agent can be NAD or NADH, nicotinamide mononucleotide, nicotinic acid mononucleotide or nicotinamide riboside or derivatives thereof; or an enzyme that generates NAD such as a nicotinamide mononucleotide adenylyltransferase or a nucleic acid encoding an enzyme that generates NAD such as a nucleic acid encoding a nicotinamide mononucleotide adenylyltransferase or an agent that increases expression of a nucleic acid encoding an enzyme in a pathway that generates NAD or an agent that increases activity and/or stability of an enzyme in a pathway that generates NAD or an agent that increases NAD activity. The nicotinamide mononucleotide adenylyltransferase can be an NMNAT1 protein.

In various embodiments, the invention can also involve methods of treating or preventing an optic neuropathy in a mammal in need thereof. The methods can comprise administering to the mammal an effective amount of an agent that acts by increasing NAD activity in diseased and/or injured neurons. Administering to the mammal can comprise administering to the eye, in particular by administering the agent with a sustained release delivery system or by administering a sustain release pellet comprising the agent to the eye.

The agent can be NAD or NADH, nicotinamide mononucleotide, nicotinic acid mononucleotide or nicotinamide riboside; or an enzyme that generates NAD such as a nicotinamide mononucleotide adenylyltransferase; or a nucleic acid encoding an enzyme that generates NAD such as a nucleic acid encoding a nicotinamide mononucleotide adenylyltransferase or an agent that increases NAD activity. The nicotinamide mononucleotide adenylyltransferase can be an NMNAT1 protein or an NMNAT3 protein.

In various embodiments of the methods of the present invention, the neuropathy associated with axonal degradation can be any of a number of neuropathies such as, for example, those that are hereditary or congenital or associated with Parkinson's disease, Alzheimer's disease, Herpes infection, diabetes, amyotrophic lateral sclerosis, a demyelinating disease, ischemia or stroke, chemical injury, thermal injury, AIDS and the like. In addition, neurodegenerative diseases not mentioned above as well as a subset of the above mentioned diseases can also be treated with the methods of the present invention. Such subsets of diseases can include Parkinson's disease or non-Parkinson's diseases, Alzheimer's disease or non-Alzheimer's diseases and so forth.

In various embodiments, the present invention is also directed to methods of screening agents for treating a neuropathy in a mammal. The methods can comprise administering to neuronal cells in vitro or in vivo, a candidate agent, producing an axonal injury to the neuronal cells and detecting a decrease in axonal degeneration of the injured neuronal cells. In various embodiments, the method can comprise detecting an increase in NAD activity produced by a candidate agent, in a cell and, in particular, in a neuronal cell. The increase in NAD activity can be an increase in nuclear NAD activity.

Methods are also provided for screening agents that increase sirtuin activity in neurons as well as for screening agents that increase NAD biosynthetic activity in neurons. The methods can comprise administering to mammalian neuronal cells in vitro or in vivo a candidate agent, producing an axonal injury to the neuronal cells and detecting a decrease in axonal degeneration of the injured neuronal cells. Such methods can in some embodiments be primary screening methods in which secondary assays further delineate activity as associated with sirtuin activity or with NAD and enzymes or components of NAD biosynthetic or salvage pathways.

In various embodiments of the screening methods of the present invention, axonal injury can be produced by a number of methods including chemically injuring the neuronal cells, thermally injuring the neuronal cells, oxygen-depriving the neuronal cells, and physically injuring the neuronal cells.

A recombinant vector is also provided in various embodiments. The vector can comprise a promoter operatively linked to a sequence encoding a mammalian NMNAT1 protein or NMNAT3 protein. In various aspects of such embodiments, the recombinant vector can be a lentivirus or an adeno-associated virus.

Also provided in various embodiments, is a recombinant vector comprising a promoter operatively linked to a sequence encoding a SIRT1 protein. In various aspects of such embodiments, the recombinant vector can be a lentivirus or an adeno-associated virus.

A) In vitro Wallerian degeneration using DRG explant cultures preincubated with 1 mM NAD alone (control) or in the presence of either 100 µM Sirtinol (a Sir2 inhibitor) or 20 mM 3-aminobenzimide (3AB, a PARP inhibitor);

B) in vitro Wallerian degeneration using DRG explant cultures incubated with resveratrol (10, 50 or 100 µM); and C) left: in vitro Wallerian degeneration using DRG explant cultures infected with lentivirus expressing siRNA specific for each member of the SIRT family (SIRT1-7) wherein the bar chart shows the quantitative analysis of the number of remaining neurites (percentage of remaining neurites relative to pre-transection±S.D.) at indicated time-point for each condition and the "*" indicates points significantly different than control (<0.0001);

middle table: The effectiveness of each SIRT siRNA (expressed as % of wild type mRNA level) using qRT-PCR in infected NIH3T3 cells; and right: immunoblot using antibodies to SIRT1 to show decreased expression of SIRT1 in the presence of SIRT1 siRNA which effectively blocked NAD dependent axonal protection.

Figure 5:
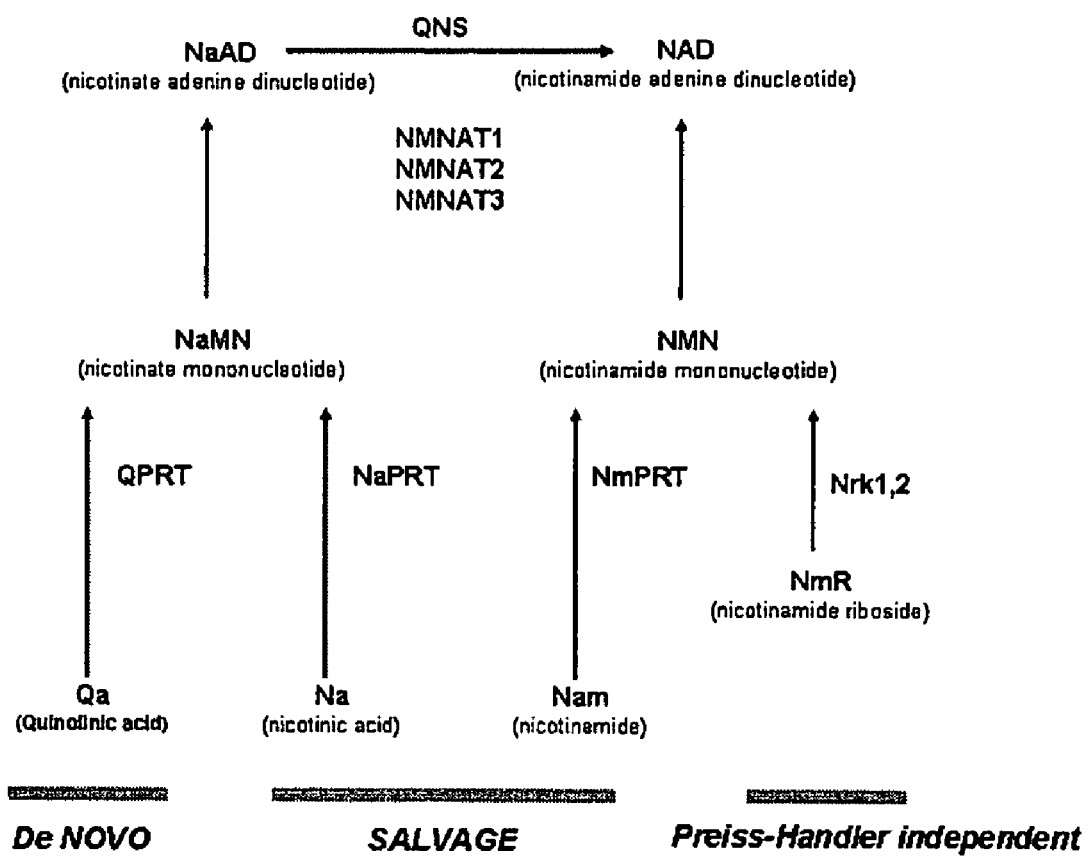

FIG. 5 illustrates the mammalian NAD biosynthetic pathway in which predicted mammalian NAD biosynthesis is illustrated based on the enzymatic expression analysis and studies from yeast and lower eukaryotes (Abbreviation used; QPRT, quinolinate phosphoribosyltransferase; NaPRT, nicotinic acid phosphoribosyltransferase; NmPRT, nicotinamide phosphoribosyltransferase; Nrk, nicotinamide riboside kinase; NMNAT, nicotinamide mononucleotide adenylyltransferase; QNS, NAD synthetase)

Figure 6:
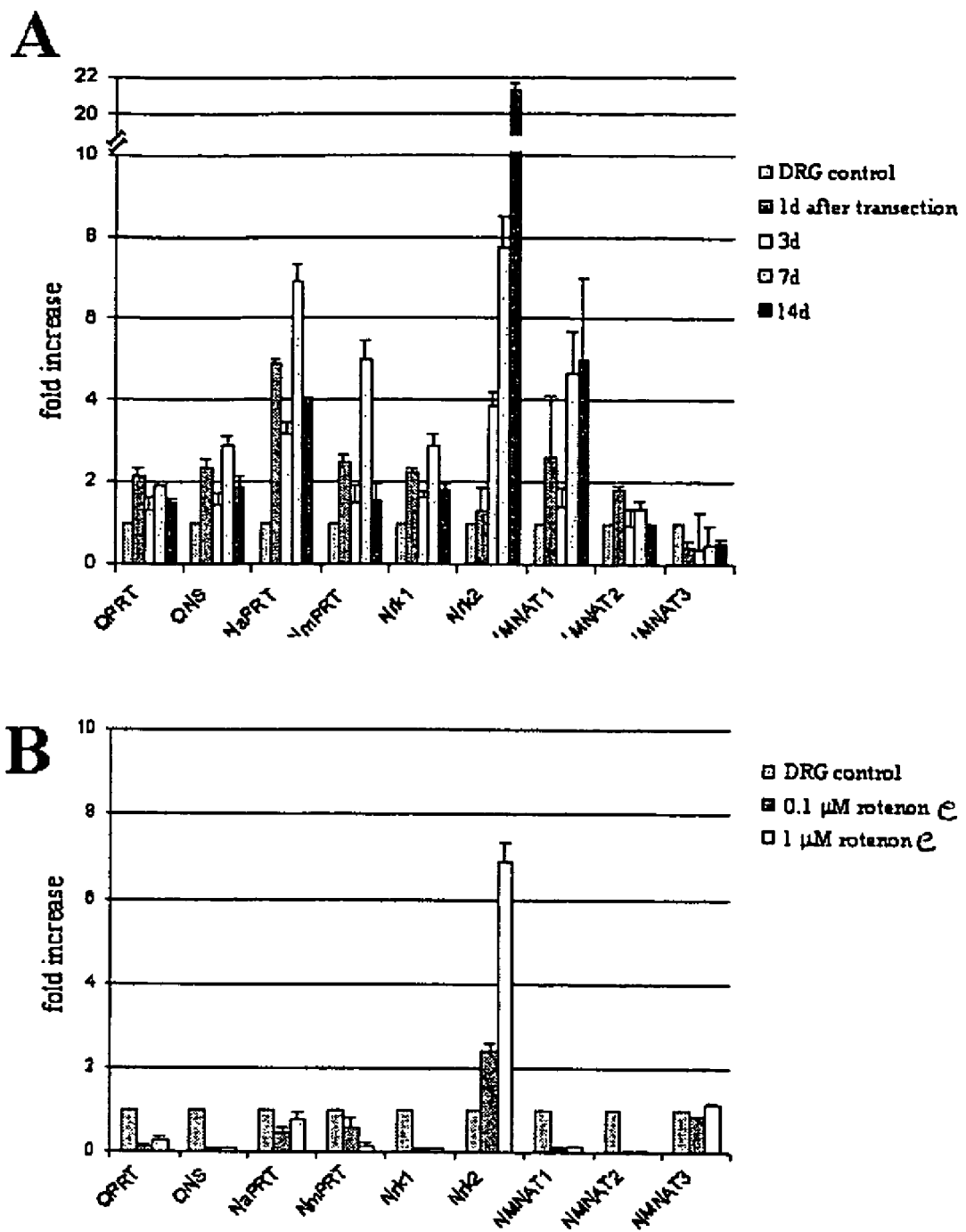

FIG. 6 illustrates expression analysis of NAD biosynthetic enzymes in mammal showing (A) NAD biosynthesis enzyme mRNA levels after 1, 3, 7, and 14 days after nerve transection in rat DRG were determined by qRT-PCR in which the expression level was normalized to glyceraldehydes-3-phosphate dehydrogenase expression in each sample and is indicated relative to the expression level in non-axotomized DRG; (B) neurite degeneration introduced by incubation DRG in 1 or 0.1 µM rotenone for indicated time and NAD synthesis enzyme mRNA levels were determined by qRT-PCR as described in the text.

Figure 7:
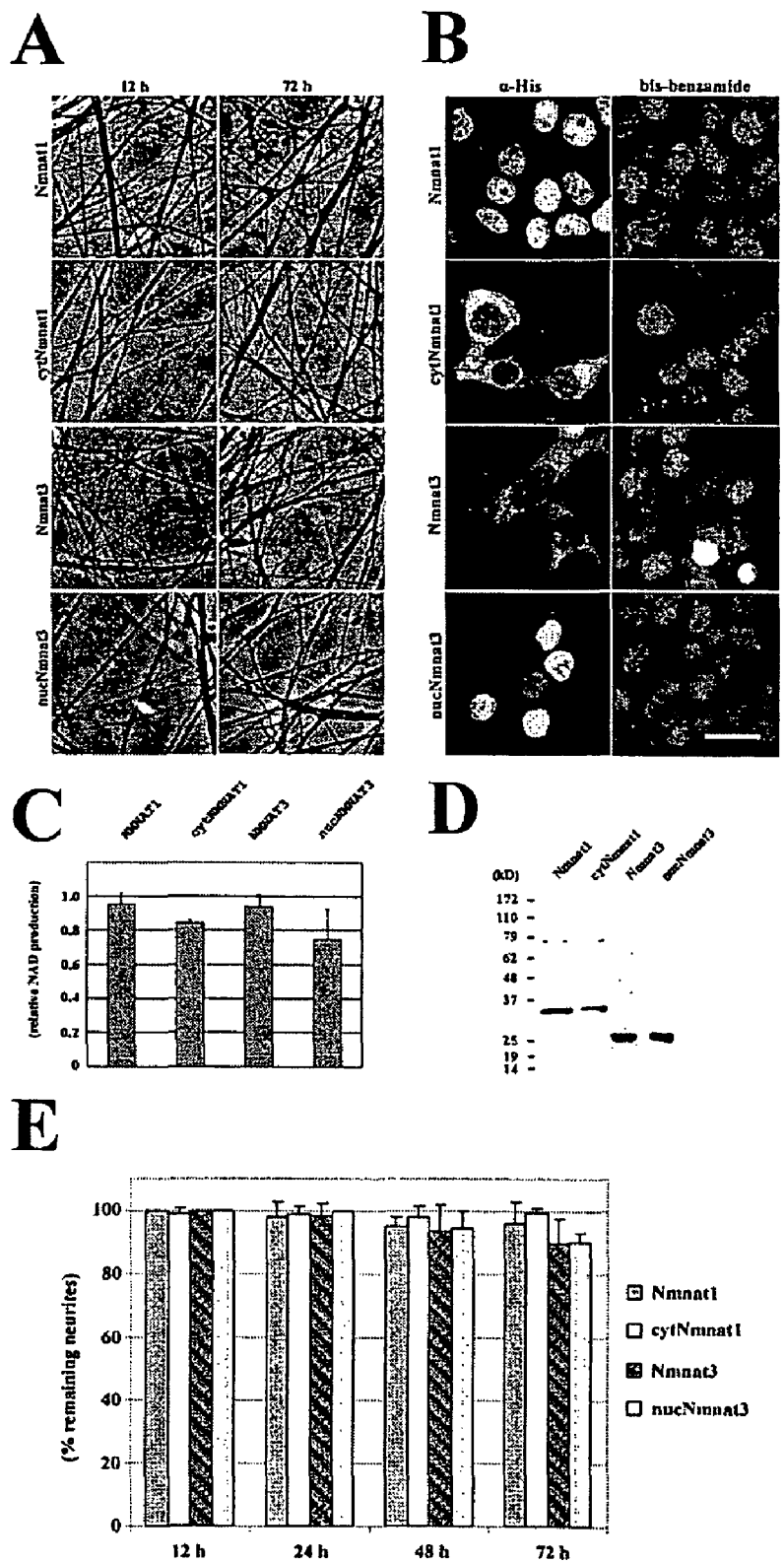

FIG. 7 illustrates the subcellular localization of NMNAT enzymes and their ability to protect axon showing (A) in vitro Wallerian degeneration assay using lentivirus infected DRG neuronal explant cultures expressing NMNAT1, cytNMNAT1, NMNAT3, or nucNMNAT3 in which representative pictures taken at 12 and 72 hours after transaction are shown; (B) Subcellular localization of NMNAT1, cytNMNAT1, NMNAT3, or nucNMNAT3 in HEK 293T cells using immunohistochemistry with antibody against 6×His tag to detect each proteins and staining of the cells with the nuclear marker dye (bisbenzimide) for comparison to determine the nuclear vs. cytoplasmic location of each protein (Scale bar=25 µm); (C) enzymatic activity of wild type and mutant NMNAT1 and NMNAT3 in which 6×His tagged each protein was purified from lysate of HEK293T cells expressing NMNAT1, cytNMNAT1, NMNAT3, nucNMNAT3 in which the amount of NAD generated after 1 hour at 37 deg was converted NADH, quantified and normalized to protein concentration; (D) protein expression of NMNAT1, cytNMNAT1, NMNAT3, and nucNMNAT3 by lentivirus gene transfer confirmed by immunoblot analysis of HEK293T cells infected with each of the virus and (E) in vitro Wallerian degeneration assay using lentivirus infected DRG neuronal explant cultures expressing NMNAT1, cytNMNAT1, NMNAT3, or nucNMNAT3 showing quantitative analysis data of remaining neurite numbers at 12, 24, 48, and 72 hours after axotomy.

Figure 8:
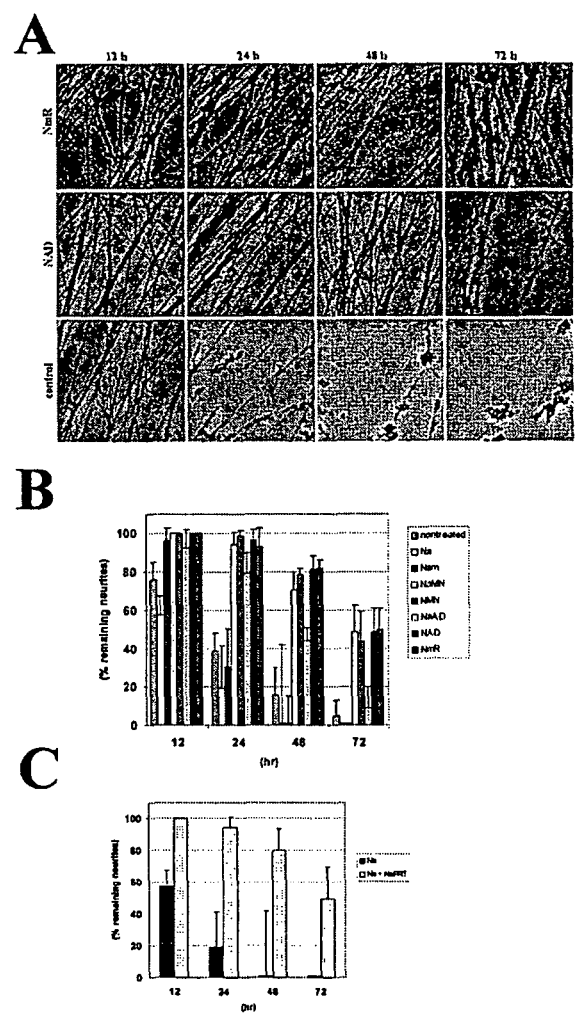

FIG. 8 illustrates exogenous application of NAD biosynthetic substrates and their ability to protect axon showing (A) in vitro Wallerian degeneration assay using DRG neuronal explant cultures after exogenous application of NAD, NmR with representative pictures taken at 12, 24, 48, and 72 hours after transaction are shown; (B) in vitro Wallerian degeneration assay using DRG neuronal explant cultures after exogenous application of Na, Nam, NaMN, NMN, NaAD, NAD, and NmR showing quantitative analysis data of remaining neurite numbers at 12, 24, 48, and 72 hours after axotomy are shown; (C) DRG neuronal explants infected with NaPRT expressing lentivirus and incubated with or without 1 mM of Na for 24 hours before axotomy, in in vitro Wallerian degeneration assay showing quantitative analysis data of remaining neurite numbers at 12, 24, 48, and 72 hours after axotomy.

Figure 9:
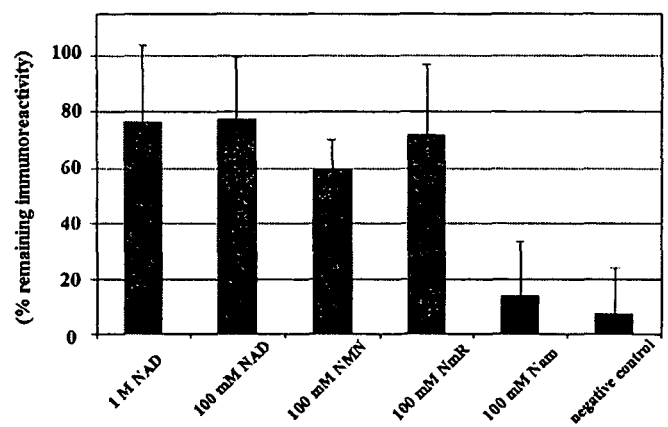

FIG. 9 illustrates optic nerve transection after intravitreal injection of NAD biosynthetic substrates NAD, NMN, NmR, or Nam was injected into intravitreal compartment of left rat eye and allowed to incorporate retinal ganglion cells for 24 hours after which, left optic nerve was transected by eye enucleation and right and left optic nerves were collected at 4 days after transection and analyzed by Western blotting in which optic nerves transected from mice without any treatment prior to axotomy were used for negative control; showing in the figure, the quantitative analysis data of percentage of remaining neurofilament immunoreactivity from transected optic nerve relative to non-transected±S.D.

DETAILED DESCRIPTION

The present invention involves methods and compositions for treating neuropathies. The methods can comprise administering to a mammal an effective amount of a substance that increases NAD activity in diseased and/or injured neurons. It is believed that the increased NAD activity can act to increase sirtuin activity which then produces a decrease in axonal degeneration of injured neuronal cells compared to axonal degeneration that occurs in injured neuronal cells not treated with the agent. Such decrease in axonal degeneration can include a complete or partial amelioration of the injury to the neuron. It is also believed possible that the increase in NAD activity could act through other mechanisms not involving sirtuin molecules to produce or to contribute to the production of a decrease in axonal degeneration.

Seven known sirtuin molecules referenced as SIRT's make up the Sir2 family of histone/protein deacetylases in mammals and all such sirtuin molecules are included within the scope of the present invention. The seven human sirtuins, SIRT1-SIRT7, are NAD-dependent histone/protein deacetylases which are described more fully in connection with NCBI LocusLink ID Nos. 23411, 22933, 23410, 23409, 23408, 51548 and 51547, respectively (see http://www.ncbi.nlm.hih.gov/LocusLink/). Said NCBI LocusLink reference sites are hereby incorporated by reference. In various embodiments, the methods and compositions of the present invention can increase activity of any one or more of the sirtuins and, in particular, various methods of the present invention increase activity of SIRT1.

By activity of a substance, reference is made to either the concentration of the particular substance or functional effectiveness of the substance. Concentration of a substance can be increased by numerous factors including, for example, increasing synthesis, decreasing breakdown, increasing bioavailability of the substance or diminishing binding of the substance or otherwise increasing the available amount of free substance. Increasing functional effectiveness can result, for example, from a change in molecular conformation, a change in the conditions under which the substance is acting, a change in sensitivity to the substance, and the like. Increasing activity with respect to sirtuin molecules is intended to mean increasing concentration or enhancing functional effectiveness or increasing the availability of NAD or increasing the flux through one or more biosynthetic pathways for NAD or any combination thereof.

Neuropathies can include any disease or condition involving neurons and/or supporting cells, such as for example, glia, muscle cells, fibroblasts, etc., and, in particular, those diseases or conditions involving axonal damage. Axonal damage can be caused by traumatic injury or by non-mechanical injury due to diseases or conditions and the result of such damage can be degeneration or dysfunction of the axon and loss of functional neuronal activity. Disease and conditions producing or associated with such axonal damage are among a large number of neuropathic diseases and conditions. Such neuropathies can include peripheral neuropathies, central neuropathies, and combinations thereof. Furthermore, peripheral neuropathic manifestations can be produced by diseases focused primarily in the central nervous systems and central nervous system manifestations can be produced by essentially peripheral or systemic diseases.

Peripheral neuropathies involve damage to the peripheral nerves and such can be caused by diseases of the nerves or as the result of systemic illnesses. Some such diseases can include diabetes, uremia, infectious diseases such as AIDs or leprosy, nutritional deficiencies, vascular or collagen disorders such as atherosclerosis, and autoimmune diseases such as systemic lupus erythematosus, scleroderma, sarcoidosis, rheumatoid arthritis, and polyarteritis nodosa. Peripheral nerve degeneration can also result from traumatic, i.e mechanical damage to nerves as well as chemical or thermal damage to nerves. Such conditions that injure peripheral nerves include compression or entrapment injuries such as glaucoma, carpal tunnel syndrome, direct trauma, penetrating injuries, contusions, fracture or dislocated bones; pressure involving superficial nerves (ulna, radial, or peroneal) which can result from prolonged use of crutches or staying in one position for too long, or from a tumor; intraneural hemorrhage; ischemia; exposure to cold or radiation or certain medicines or toxic substances such as herbacides or pesticides. In particular, the nerve damage can result from chemical injury due to a cytotoxic anticancer agent such as, for example, a vinca alkaloid such as vincristine. Typical symptoms of such peripheral neuropathies include weakness, numbness, paresthesia (abnormal sensations such as burning, tickling, pricking or tingling) and pain in the arms, hands, legs and/or feet. The neuropathy can also be associated with mitochondrial dysfunction. Such neuropathies can exhibit decreased energy levels, i.e. decreased levels of NAD and ATP.

The peripheral neuropathy can also be a metabolic and endocrine neuropathy which includes a wide spectrum of peripheral nerve disorders associated with systemic diseases of metabolic origin. These diseases, some of which are mentioned earlier, include diabetes mellitus, hypoglycemia, uremia, hypothyroidism, hepatic failure, polycythemia, amyloidosis, acromegaly, porphyria, disorders of lipid/glycolipid metabolism, nutritional/vitamin deficiencies, and mitochondrial disorders, among others. The common hallmark of these diseases is involvement of peripheral nerves by alteration of the structure or function of myelin and axons due to metabolic pathway dysregulation.

Neuropathies also include optic neuropathies such as glaucoma; retinal ganglion degeneration such as those associated with retinitis pigmentosa and outer retinal neuropathies; optic nerve neuritis and/or degeneration including that associated with multiple sclerosis; traumatic injury to the optic nerve which can include, for example, injury during tumor removal; hereditary optic neuropathies such as Kjer's disease and Leber's hereditary optic neuropathy; ischemic optic neuropathies, such as those secondary to giant cell arteritis; metabolic optic neuropathies such as neurodegenerative diseases including Leber's neuropathy mentioned earlier, nutritional deficiencies such as deficiencies in vitamins B12 or folic acid, and toxicities such as due to ethambutol or cyanide; neuropathies caused by adverse drug reactions and neuropathies caused by vitamin deficiency. Ischemic optic neuropathies also include non-arteritic anterior ischemic optic neuropathy.

Neurodegenerative diseases that are associated with neuropathy or axonopathy in the central nervous system include a variety of diseases. Such diseases include those involving progressive dementia such as, for example, Alzheimer's disease, senile dementia, Pick's disease, and Huntington's disease; central nervous system diseases affecting muscle function such as, for example, Parkinson's disease, motor neuron diseases and progressive ataxias such as amyotrophic lateral sclerosis; demyelinating diseases such as, for example multiple sclerosis; viral encephalitides such as, for example, those caused by enteroviruses, arboviruses, and herpes simplex virus; and prion diseases. Mechanical injuries such as glaucoma or traumatic injuries to the head and spine can also cause nerve injury and degeneration in the brain and spinal cord. In addition, ischemia and stroke as well as conditions such as nutritional deficiency and chemical toxicity such as with chemotherapeutic agents can cause central nervous system neuropathies.

The term "treatment" as used herein is intended to include intervention either before or after the occurrence of neuronal injury. As such, a treatment can prevent neuronal injury by administration before a primary insult to the neurons occurs as well as ameliorate neuronal injury by administration after a primary insult to the neurons occurs. Such primary insult to the neurons can include or result from any disease or condition associated with a neuropathy. "Treatment" also includes prevention of progression of neuronal injury. "Treatment" as used herein can include the administration of drugs and/or synthetic substances, the administration of biological substances such as proteins, nucleic acids, viral vectors and the like as well as the administration of substances such as neutraceuticals, food additives or functional foods.

The methods and compositions of the present invention are useful in treating mammals. Such mammals include humans as well as non-human mammals. Non-human mammals include, for example, companion animals such as dogs and cats, agricultural animals such live stock including cows, horses and the like, and exotic animals, such as zoo animals.

Substances that can increase sirtuin activity in mammals can include polyphenols some of which have been described earlier (see for example Howitz et al., *Nature* 425:191-196, 2003 and supplementary information that accompanies the paper all of which is incorporated herein by reference). Such compounds can include stilbenes such as resveratrol, piceatannol, deoxyrhapontin, trans-stilbene and rhapontin; chalcone such as butein, isoliquiritigen and 3,4,2',4',6'-pentahydroxychalcone and chalcone; flavones such as fisetin, 5,7,3', 4',5'-pentahydroxyflavone, luteolin, 3,6,3',4'-tetrahydroxyflavone, quercetin, 7,3',4',5'-tetrahydroxyflavone, kaempferol, 6-hydroxyapigenin, apigenin, 3,6,2',4'-tetrahydroxyflavone, 7,4'-dihydroxyflavone, 7,8,3',4'-tetrahydroxyflavone, 3,6,2',3'-tetrahydroxyflavone, 4'-hydroxyflavone, 5,4'-dihydroxyflavone, 5,7-dihydroxyflavone, morin, flavone and 5-hydroxyflavone; isoflavones such as daidzein and genistein; flavanones such as naringenin, 3,5,7,3',4'-pentahydroxyflavanone, and flavanone or catechins such as (−)-epicatechin, (−)-catechin, (−)-gallocatechin, (+)-catechin and (+)-epicatechin.

Additional polyphenols or other substance that increase sirtuin deacetylase activity can be identified using assay systems described herein as well as in commercially available assays such as fluorescent enzyme assays (Biomol International L.P., Plymouth Meeting, Pa.). Sinclair et al. also disclose substances that can increase sirtuin activity (Sinclair et al., WO2005/02672 which is incorporated in its entirety by reference).

In various embodiments, other substances can increase sirtuin activity indirectly by increasing NAD activity as a result of the particular sirtuin functioning through NAD-dependent histone/protein deacetylase activity. NAD activity can be increased by administration of NAD or NADH as well as by synthesizing NAD. NAD can be synthesised through three major pathways, the de novo pathway in which NAD is synthesized from tryptophan, the NAD salvage pathway in which NAD is generated by recycling degraded NAD products such as nicotinamide (Lin et al. *Curent Opin. Cell Biol.* 15:241-246, 2003; Magni et al., *Cell Mol. Life Sci.* 61:19-34, 2004) and the nicotinamide riboside kinase pathway in which nicotinamide riboside is converted to nicotinamide mononucleotide by nicotinamide riboside kinase (Bieganowski et al., *Cell* 117:495-502, 2004). Thus, administering to injured neurons, a precursor of NAD in the de novo pathway such as, for example, tryptophan or nicotinate and/or substances in the NAD salvage pathway such as, for example, nicotinamide, nicotinic acid, nicotinic acid mononucleotide, or deamido-NAD and/or substances in the nicotinamide riboside kinase pathway such as, for example, nicotinamide riboside or nicotinamide mononucleotide, could potentially increase NAD activity. As shown below, nicotinamide mononucleotide, nicotinic acid mononucleotide or nicotinamide riboside, in addition to NAD, protected against axonal degeneration to a similar extent as did NAD, however, nicotinic acid and nicotinamide did not. The increased NAD activity can then increase sirtuin histone/protein deacetylase activity in the injured neurons and diminish or prevent axonal degeneration. In addition, it is believed that other substances can act by increasing enzyme activity or by increasing levels of NAD, nicotinamide mononucleotide, nicotinic acid mononucleotide, nicotinamide riboside or sirtuin enzymes or by decreasing degradation of NAD, nicotinamide mononucleotide, nicotinic acid mononucleotide, nicotinamide riboside or sirtuin enzymes.

In various embodiments, NAD can be increased in injured neurons by administering enzymes that synthesize NAD or nucleic acids comprising enzymes that synthesize NAD. Such enzymes can include an enzyme in the de novo pathway for synthesizing NAD, an enzyme of the NAD salvage pathway or an enzyme of the nicotinamide riboside kinase pathway or a nucleic acid encoding an enzyme in the de novo pathway for synthesizing NAD, an enzyme of the NAD salvage pathway or an enzyme of the nicotinamide riboside kinase pathway and, in particular, an enzyme of the NAD salvage pathway such as, for example, a nicotinamide mononucleotide adenylyltransferase (NMNAT) such as NMNAT1. Thus, in one non-limiting example, administration of an NMNAT such as NMNAT1 or NMNAT3 or a nucleic acid comprising a sequence encoding an NMNAT such as NMNAT1 or NMNAT3 can diminish or prevent axonal degeneration in injured neurons.

The human NMNAT1 enzyme (E.C.2.7.7.18) is represented according to the GenBank Assession numbers for the human NMNAT1 gene and/or protein:NP_073624; NM_022787; AAL76934; AF459819; and NP_073624; AF314163. A variant of this gene is NMNAT-2 (KIAA0479), the human version of which can be found under GenBank Accession numbers NP_055854 and NM_015039.

As used herein, the term "percent identical" or "percent identity" or "% identity" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases. Databases with individual sequences are described in Methods in Enzymology, ed. Doolittle, supra. Databases include Genbank, EMBL, and DNA Database of Japan (DDBJ).

A "variant" of a polypeptide refers to a polypeptide having the amino acid sequence of the polypeptide in which is altered in one or more amino acid residues. The variant may have "conservative" changes, wherein a substituted amino acid has similar structural or chemical properties (e.g., replacement of leucine with isoleucine). A variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to that of a particular gene or the coding sequence thereof. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variation is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

An agent that can be used in treating or preventing a neuropathy in accordance with the methods and compositions of the present invention can be comprised by a nicotinamide mononucleotide adenylyltransferase (NMNAT) or a polynucleotide encoding an NMNAT. In particular, the agent can be an enzyme having NMNAT activity and at least 50% identity with a human NMNAT1 or at least 50% identity with a human NMNAT3, at least 60% identity with a human NMNAT1 or at least 60% identity with a human NMNAT3, at least identity with a human NMNAT1 or at least 70% identity with a human NMNAT3, at least 80% identity with a human NMNAT1 or at least 80% identity with a human NMNAT3, at least 90% identity with a human NMNAT1 or at least 90% identity with a human NMNAT3, at least 95% identity with a human NMNAT1 or at least 95% identity with a human NMNAT3. Moreover, the agent can be comprised by a human NMNAT1, a human NMNAT3 or a conservatively substituted variants thereof.

The agent can also be comprised by a polynucleotide having at least 50% identity with a nucleic acid encoding a human NMNAT1 or a polynucleotide having at least 50% identity with a nucleic acid encoding a human NMNAT3, a polynucleotide having at least 60% identity with a nucleic acid encoding a human NMNAT1 or a polynucleotide having at least 60% identity with a nucleic acid encoding a human NMNAT3, a polynucleotide having at least 70% identity with a nucleic acid encoding a human NMNAT1 or a polynucleotide having at least 70% identity with a nucleic acid encoding a human NMNAT3, a polynucleotide having at least 80% identity with a nucleic acid encoding a human NMNAT1 or a polynucleotide having at least 80% identity with a nucleic acid encoding a human NMNAT3, a polynucleotide having at least 90% identity with a nucleic acid encoding a human NMNAT1 or a polynucleotide having at least 90% identity with a nucleic acid encoding a human NMNAT3, a polynucleotide having at least 95% identity with a nucleic acid encoding a human NMNAT1 or a polynucleotide having at least 95% identity with a nucleic acid encoding a human NMNAT3. The agent can also be a polynucleotide encoding a human NMNAT1, a human NMNAT3 or a variant thereof.

The agent can also be comprise by a sirtuin polypeptide or a nucleic acid encoding a sirtuin polypeptide. In particular, the agent can comprise an enzyme having SIRT activity and at least 50% identity with a human SIRT1, at least 60% identity with a human SIRT1, at least 70% identity with a human SIRT1, at least 80% identity with a human SIRT1, at least 90% identity with a human SIRT1, or at least 95% identity with a human SIRT1. Moreover, the agent can be comprised by a human SIRT1 or a conservatively substituted variants thereof. The agent can also be comprised by a polynucleotide having at least 50% identity with a nucleic acid encoding a human SIRT1, a polynucleotide having at least 60% identity with a nucleic acid encoding a human SIRT1, a polynucleotide having at least 70% identity with a nucleic acid encoding a human SIRT1, a polynucleotide having at least 80% identity with a nucleic acid encoding a human SIRT1, a polynucleotide having at least 90% identity with a nucleic acid encoding a human SIRT1 or a polynucleotide having at least 95% identity with a nucleic acid encoding a human SIRT1. Moreover, the agent can comprise a polynucleotide encoding a human SIRT1 or a variant thereof.

Administration can be by any suitable route of administration including buccal, dental, endocervical, intramuscular, inhalation, intracranial, intralymphatic, intramuscular, intraocular, intraperitoneal, intrapleural, intrathecal, intratracheal, intrauterine, intravascular, intravenous, intravesical, intranasal, ophthalmic, oral, otic, biliary perfusion, cardiac perfusion, priodontal, rectal, spinal subcutaneous, sublingual, topical, intravaginal, transermal, ureteral, or urethral. Dosage forms can be aerosol including metered aerosol, chewable bar, capsule, capsule containing coated pellets, capsule containing delayed release pellets, capsule containing extended release pellets, concentrate, cream, augmented cream, suppository cream, disc, dressing, elixer, emulsion, enema, extended release fiber, extended release film, gas, gel, metered gel, granule, delayed release granule, effervescent granule, chewing gum, implant, inhalant, injectable, injectable lipid complex, injectable liposomes, insert, extended release insert, intrauterine device, jelly, liquid, extended release liquid, lotion, augmented lotion, shampoo lotion, oil, ointment, augmented ointment, paste, pastille, pellet, powder, extended release powder, metered powder, ring, shampoo, soap solution, solution for slush, solution/drops, concentrate solution, gel forming solution/drops, sponge, spray, metered spray, suppository, suspension, suspension/drops, extended release suspension, swab, syrup, tablet, chewable tablet, tablet containing coated particles, delayed release tablet, dispersible tablet, effervescent tablet, extended release tablet, orally disintegrating tablet, tampon, tape or troche/lozenge.

Intraocular administration can include administration by injection including intravitreal injection, by eyedrops and by trans-scleral delivery.

Administration can also be by inclusion in the diet of the mammal such as in a functional food for humans or companion animals.

It is also contemplated that certain formulations containing the compositions that increase sirtuin activity are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and promote absorption such as, for example, surface active agents.

The specific dose can be calculated according to the approximate body weight or body surface area of the patient or the volume of body space to be occupied. The dose will also depend upon the particular route of administration selected. Further refinement of the calculations necessary to determine the appropriate dosage for treatment is routinely made by those of ordinary skill in the art. Such calculations can be made without undue experimentation by one skilled in the art in light of the activity in assay preparations such as has been described elsewhere for certain compounds (see for example, Howitz et al., *Nature* 425:191-196, 2003 and supplementary information that accompanies the paper). Exact dosages can be determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

In various embodiments, the present invention also provides methods of screening candidate agents. In one such assay method, agents are tested for effectiveness in decreasing or preventing axonal degeneration of injured neuronal cells. Candidate agents are thus administered to neuronal cells subjected to injury and a decrease in axonal degeneration of the injured neuronal cells is detected. Typically, the agent is added prior to producing the injury, however, in some instances, the injury can be produced before addition of the candidate compound. The method can be performed in vitro or in vivo. The in vitro tests can be performed using any of a number of mammalian neuronal cells under a variety of experimental conditions in which injury is elicited. An example of mammalian neuronal cell-types that can be used are primary dorsal root ganglion cells injured by either transection and removal of the neuronal cell body or growth in media containing vincristine as described below. The in vivo tests can be performed in intact animals such as, for example, a mouse model of peripheral nerve regeneration (Pan et al., *J. Neurosci.* 23:11479-11488, 2003) or mouse model of progressive motor neuronopathy (Schmalbruch et al., *J. Neuropathol. Exp. Neurol.* 50:192-204, 1991; Ferri et al., *Current Biol.* 13:669-673, 2003).

Because, the mechanism of decreasing or preventing neuronal injury results from an increase in NAD-dependent histone/protein deacetylase activity of sirtuin molecules, the assay method can also be used as a primary screen for substances that either increase sirtuin activity directly or through increasing NAD activity. Thus the methods above can be used to screen for agents that increase NAD biosynthetic activity or agents that increase sirtuin activity in neurons.

Recombinant vectors that serve as carriers for a nucleic acid encoding a sirtuin molecule or an enzyme for biosynthesis of NAD are also within the scope of the present invention. Such recombinant vectors can comprise a promoter operatively linked to a sequence encoding a mammalian NMNAT1 protein or a mammalian sirtuin protein such as a SIRT1 protein. Such recombinant vectors can be any suitable vector such as, for example a lentivirus or an adeno-associated virus. Any suitable promoter can be also used such as, for example a ubiquitin promoter, a CMV promoter or a β-actin promoter.

The invention can be further understood by reference to the examples which follow.

Example 1

This example demonstrates that transected axons from neurons transfected with a vector expressing Wld$^s$ protein show a delayed degeneration compared to control neurons.

In wld$^s$ mice, Wallerian degeneration in response to axonal injury has been shown to be delayed (Gillingwater, et al., *J Physiol*, 534:627-639, 2001). Genetic analysis has shown that the wld$^s$ mutation comprises an 85 kb tandem triplication, which results in overexpression of a chimeric nuclear molecule (Wld$^s$ protein). This protein is composed of the N-terminal 70 AAs of Ufd (ubiquitin fusion degradation protein) 2a, a ubiquitin chain assembly factor, fused to the complete sequence of nicotinamide mononucleotide adenylyltransferase1 (NMNAT1), an enzyme in the NAD salvage pathway that generates NAD within the nucleus. The Wld$^s$ protein has NMNAT activity but lacks ubiquitin ligase function, suggesting that axonal protection is derived from either increased NMNAT1 activity or a 'dominant negative' inhibition of Ufd2a function.

To identify the mechanism of delayed axonal degeneration mediated by the Wld$^s$ protein, we employed an in-vitro Wallerian degeneration model. Primary DRG explant neurons were infected with lentivirus expressing the appropriate proteins, and axons were injured by either removal of the neuronal cell body (transection) or growth in vincristine (toxic).

Lentiviral expression constructs were kindly provided by D. Baltimore (Lois, et al., *Science* 295:868-72, 2002). We modified the FUGW vector to generate a general expression shuttle FUIV (ubiquitin promoter—gene of interest-IRES-enhanced YFP (Venus)) vector that enables enhanced YFP expression in cells that express the gene-of-interest. The following proteins, each with a hexahistidine tag at the C-terminus, were cloned into the FUIV vector: Wld$^s$ chimeric mutant protein; Ufd2a containing a point mutation (P1140A), which has previously been shown to inhibit wild-type Ufd2a function as a "dominant-negative" (Ufd2a(P1140)). The following genes were cloned into FUGW vector: 1) The first 70 AAs of Ufd2a (the portion contained in Wld$^s$ protein) fused to the N-terminus of EGFP (Ufd2a(1-70)-EGFP) or EGFP with nuclear localization signal at the C-terminal (Ufd2a(1-70)-nucEGFP). 2) The NMNAT1 portion of Wld$^s$ protein fused to the C-terminus of EGFP (EGFP-NMNAT1).

The murine cDNA for Ufd2a/Ube4b (mKIAA0684) was provided by Kazusa DNA Research Institute. Murine cDNAs for NMNAT1 (accession number: BC038133) were purchased from ATCC. PCR-mediated mutagenesis was used to generate point mutations in Ufd2a, NMNAT1 and Wld$^s$.

We generated siRNA constructs in the FSP-si vector generated from the FUGW backbone by replacing the ubiquitin promoter and GFP cDNA with the human U6 promoter and Pol I termination signal followed by the SV40 promoter-puromycin-N-acetyl-transferase gene. Cloning of siRNA construct was performed as described previously, so that the siRNA is transcribed from the U6 promoter (Castanotto, et al., *RNA*, 8:1454-60, 2002). Sequences used for siRNA downregulation of protein expression were 1692~1710 of SIRT1, 1032~1050 of SIRT2, 538~556 of SIRT3, 1231~1249 of SIRT4, 37~55 of SIRT5, 1390~1408 of SIRT6, and 450~468 of SIRT7. The integrity of each lentiviral expression and siRNA construct was confirmed by DNA sequencing.

Mouse DRG explants from E12.5 embryos were cultured in the presence of 1 nM nerve growth factor. Non-neuronal cells were removed from the cultures by adding 5-fluorouracil to the culture medium. Transection of neurites was performed at 10-20 DIV using an 18-gauge needle to remove the neuronal cell bodies. Incubation with β-nicotinamide adenine dinucleotide (Sigma) or Sirtinol (Calbiochem) was performed using conditions indicated in the text or figures.

Lentiviral expression vectors were generated using HEK293T cells as described above. For confirmation of lentivirus-derived protein expression, HEK293T cells were infected with lentivirus and cells were lysed 3 days after infection. These lysates were analyzed by immunoblot to using anti-His tag monoclonal antibody (Qiagen) to detect expression of the respective hexahistidine-tagged proteins. Lentiviral infection of DRG neurons was performed by incubating ~$10^6$-$10^7$ pfu/ml virus with the DRG explant for 24 h beginning 3-7 days prior to axonal transection. The infected neurons were examined under an inverted fluorescent microscope to insure detectable lentivirus-mediated transgene expression in >95% of neurons.

Quantitative analysis of axonal degeneration was performed as previously described (Zhai, et al., Neuron 39:217-25, 2003). Briefly, the cultures were examined using phase contrast microscopy at the indicated times. Axons with a fragmented, non-refractile appearance were designated as "degenerated." At each time point, at least 200 singly distinguishable axons were blindly scored from several randomly taken images of each culture. Each condition was tested in triplicate explants in each experiment. Results were obtained from 2-4 independent experiments for each condition. Statistical analysis was performed by Student's T test. For calculations of neurite-covered area, digitally captured images from quadruplicate samples of two independent experiments were analyzed using analysis 3.1 software (Soft Imaging System, Lakewood, Colo.).

Figure 1:
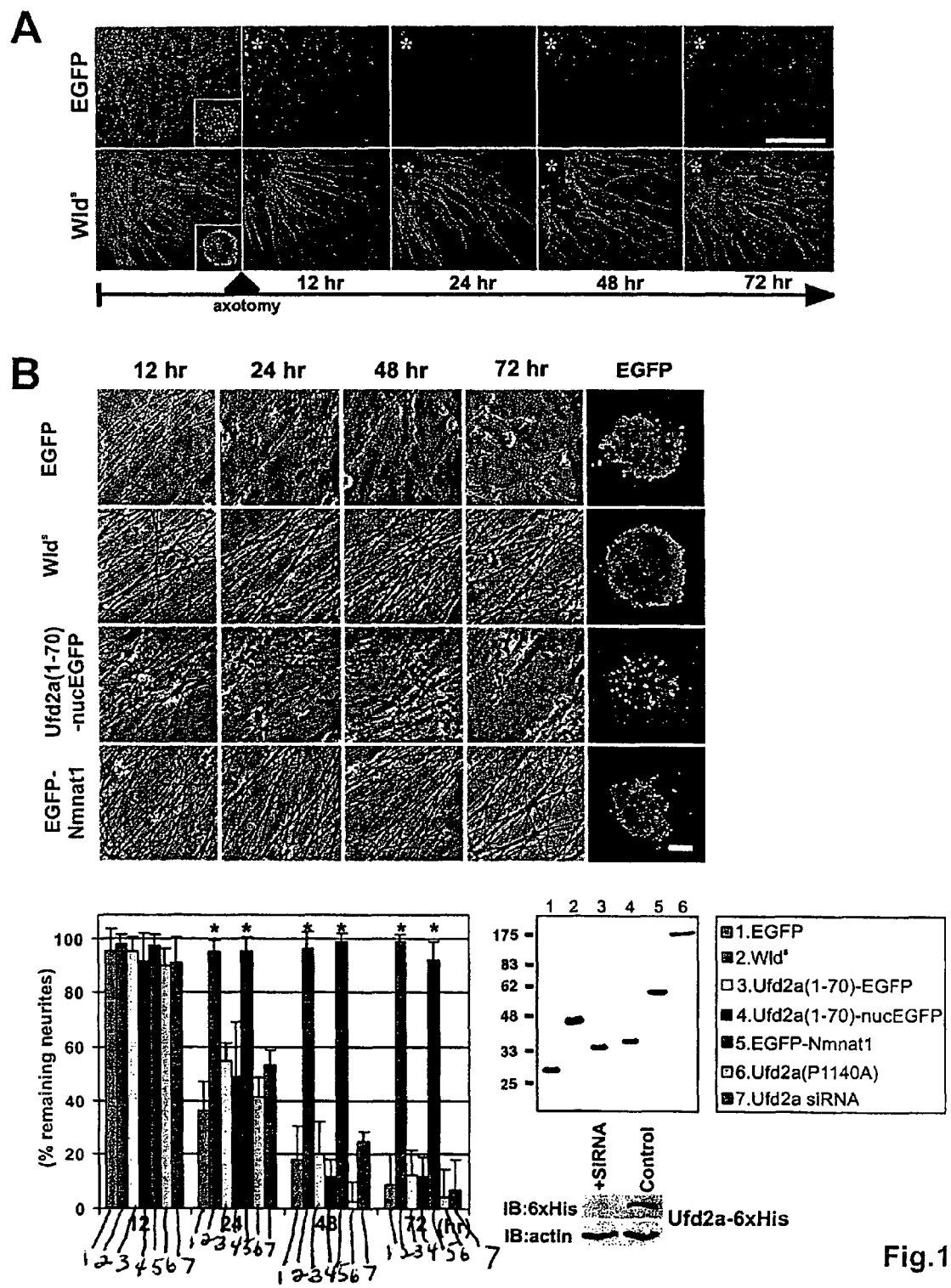
FIG. 1 illustrates that NMNAT1 activity of the Wld$^s$ fusion protein produces a delayed degeneration of injured axons showing:
A) in vitro Wallerian degeneration in lentivirus-infected dorsal root ganglia (DRG) neuronal explant cultures expressing Wld$^s$ protein or EGFP wherein tubulin βIII-immunoreactive neurites are shown before transection and 12, 24, 48, and 72 hr after transection (Scale Bar=1 mm and the "*" denotes the location of the cell bodies prior to removal; and
B) in vitro Wallerian degeneration in lentivirus-infected DRG neurons expressing EGFP only, Wld$^s$ protein, Ufd2a portion (70 residues) of Wld$^s$ protein fused to EGFP (Ufd2a(1-70)-EGFP), Ufd2a(1-70)-EGFP with C-terminal nuclear localization signal, NMNAT1 portion of Wld$^s$ protein fused to EGFP, dominant-negative Ufd2a (Ufd2a(P1140A)), or Ufd2a siRNA construct in which representative images of neurites and quantitative analysis data of remaining neurite numbers (percentage of remaining neurites relative to pre-transection±S.D.) at the indicated time-point with each construct (bottom left) are shown and the "*" indicates significant difference ($p<0.0001$) with EGFP-infected neurons; also showing EGFP signal before transection confirming transgene expression (bottom row; Scale bar=50 μm) and immunoblot analysis confirming protein expression by lentiviral gene transfer and siRNA downregulation of Ufd2a protein (bottom right panels).

We found that transected axons from neurons expressing the Wld$^s$ protein degenerated with the delayed kinetics characteristic of neurons derived from wld$^s$ (Buckmaster, et al., Eur J Neurosci 7:1596-602, 1995) mice as shown in FIG. 1A.

Next, we compared axonal degeneration after transection in neurons that overexpress Wld$^s$ protein with those that express the Ufd2a or NMNAT1 portions that make up the Wld$^s$ protein linked to EGFP. Results are shown in FIG. 1B.

We found that expression of EGFP-NMNAT1 delayed axonal degeneration comparable to Wld$^s$ protein itself, whereas the N-terminal 70 AA of Ufd2a (fused to EGFP), either targeted to the nucleus or cytoplasm, did not affect axonal degeneration. Quantification of these effects was performed by counting the percentage of remaining neurites at various times after removal of neuronal cell bodies. This analysis showed that EGFP-NMNAT1, like Wld$^s$ protein itself, resulted in a >10-fold increase in intact neurites 72 hr after injury. To further exclude direct involvement of the UPS in Wld$^s$ protein-mediated axonal protection, we examined the effect of Ufd2a inhibition using either a dominant-negative Ufd2a mutant or an Ufd2a siRNA construct. However, neither of these methods resulted in delayed axonal degradation in response to axotomy. Together, these experiments demonstrated that the NMNAT1 portion of the Wld$^s$ protein is responsible for the delayed axonal degeneration observed in wld$^s$ mice.

Example 2

This example shows that mutations in the full length NMNAT1 and in Wld$^s$ protein abolish the axonal protective effects of the proteins.

Figure 2:
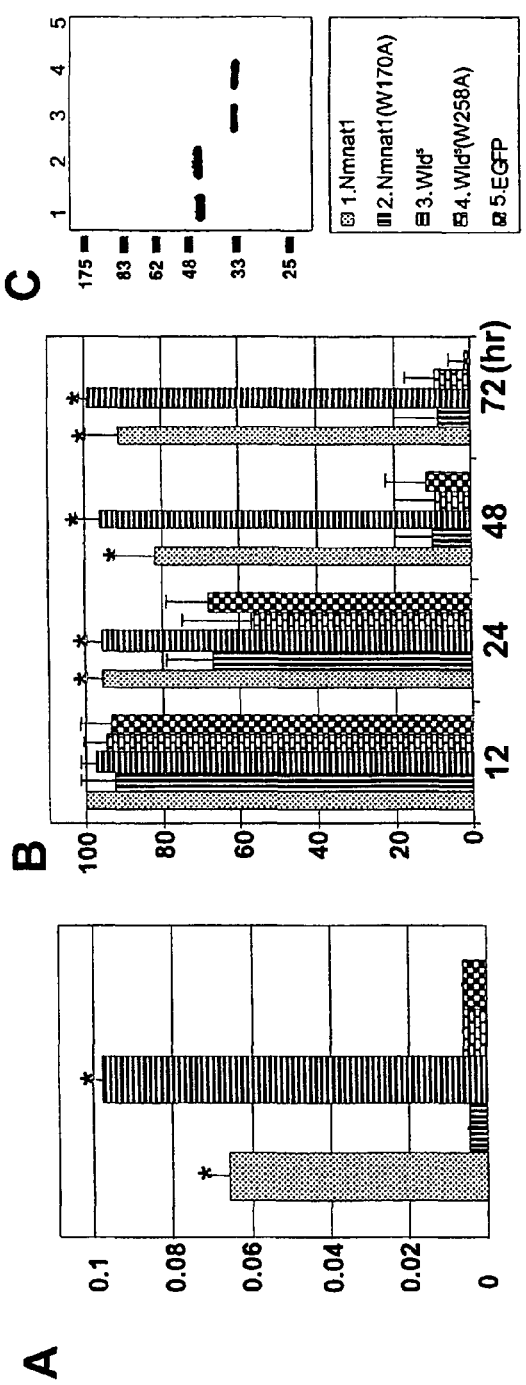
FIG. 2 illustrates that increased NAD supply protects axons from degeneration after injury showing:
A) Enzymatic activity of wild type and mutant Wld$^s$ and NMNAT1 proteins in which lysates were prepared from HEK293 cells expressing the indicated protein were assayed for NAD production using nicotinamide mononucleotide as a substrate and the amount of NAD generated in 1 h was converted to NADH, quantified by fluorescence intensity, and normalized to total protein concentration showing that both mutants have essentially no enzymatic activity; and
B) In vitro Wallerian degeneration in lentivirus-infected DRG neurons expressing NMNAT1 or Wld$^s$ protein, mutants of these proteins that lack NAD-synthesis activity NMNAT1(W170A) and Wld$^s$ (W258A), or EGFP wherein the bar chart shows the quantitative analysis data of the number of remaining neurites at indicated time-point for each construct (percentage of remaining neurites relative to pre-transection±S.D.) and the "*" indicates significant difference ($p<0.0001$) with EGFP-infected neurons;
C) Protein expression in lentivirus-infected cells detected by immunoblot analysis using antibodies to the 6×His tag; and
D) DRG neuronal explant expressing either NMNAT1 or EGFP (control) cultured with 0.5 μM vincristine wherein representative images of neurites (phase-contrast; Bar=1 mm) are shown at the indicated times after vincristine addition and quantification of the protective effect at the indicated time points is plotted as the area covered by neurites relative to that covered by neurites prior to treatment.
Figure 2:
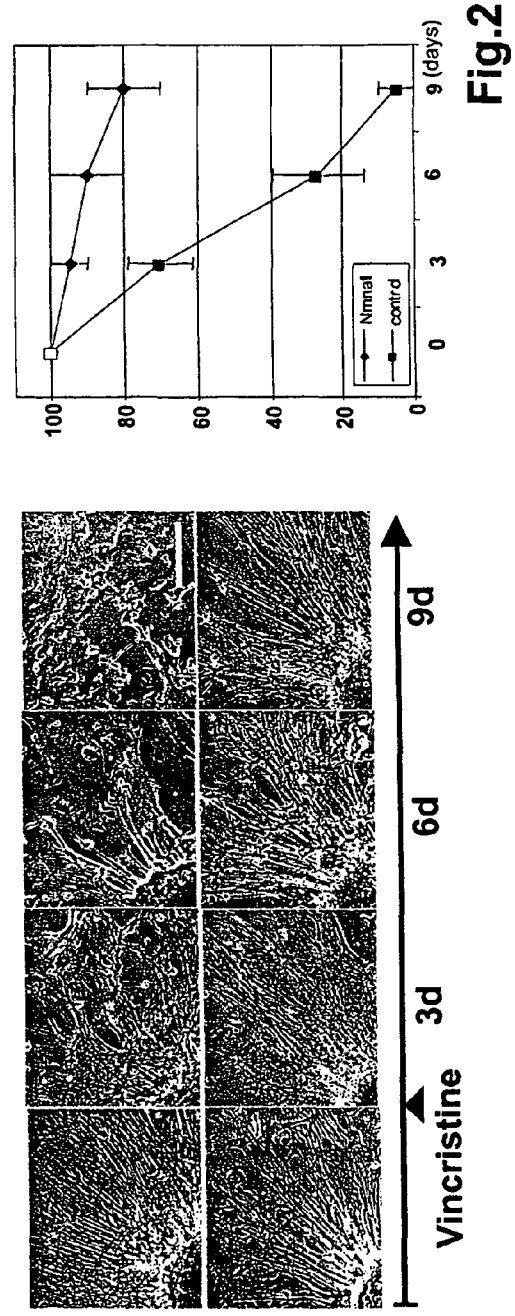

NMNAT1 is an enzyme in the nuclear NAD salvage pathway that catalyzes the conversion of nicotinamide mononucleotide (NMN) and nicotinate mononucleotide (NaMN) to NAD and nicotinate adenine mononucleotide (NaAD), respectively. The axonal protection observed in NMNAT1 overexpressing neurons could be mediated by its ability to synthesize NAD (i.e. its enzymatic activity), or perhaps, by other unknown functions of this protein. To address this question, we used the NMNAT1 crystal structure to identify several residues predicted to participate in substrate binding. A mutation in one of these residues (W170A) was engineered into full length NMNAT1 and Wld$^s$ protein. In vitro enzymatic assays confirmed that both of these mutant proteins were severely limited in their ability to synthesize NAD (FIG. 2A). Each of these mutants and their respective wild type counterparts were introduced into neurons to assess their ability to protect axons from degradation. We found that neurons expressing these enzymatically inactive mutants had no axonal protective effects (FIG. 2A), indicating that NAD/NaAD-production is responsible for the ability of NMNAT1 to prevent axonal degradation.

Example 3

This example illustrates that increased NMNAT activity in neurons injured with vincristine also show a delayed axonal degradation.

In addition to mechanical transection, axonal protection in wld$^s$ mice is also observed against other damaging agents such as ischemia and toxins (Coleman, et al., Trends Neurosci 25:532-37, 2002; Gillingwater, et al., J Cereb Blood Flow Metab 24:62-66, 2004). We sought to determine whether increased NMNAT activity would also delay axonal degradation in response to other types of axonal injury such as vincristine, a cancer chemotherapeutic reagent with well-characterized axonal toxicity. Neurons expressing either NMNAT1 or EGFP (control) were grown in 0.5 µM vincristine for up to 9 d. We found that axons of neurons expressing NMNAT1 maintained their original length and refractility, whereas axons emanating from neurons expressing EGFP gradually retracted and had mostly degenerated by day 9 (FIG. 2B). These results indicate that NMNAT activity by itself can protect axons from a number of insults and mediate the protective effects observed in wld$^s$ mice.

Example 4

This example shows that exogenously administered NAD can protect injured neurons from axonal degeneration.

Figure 3:
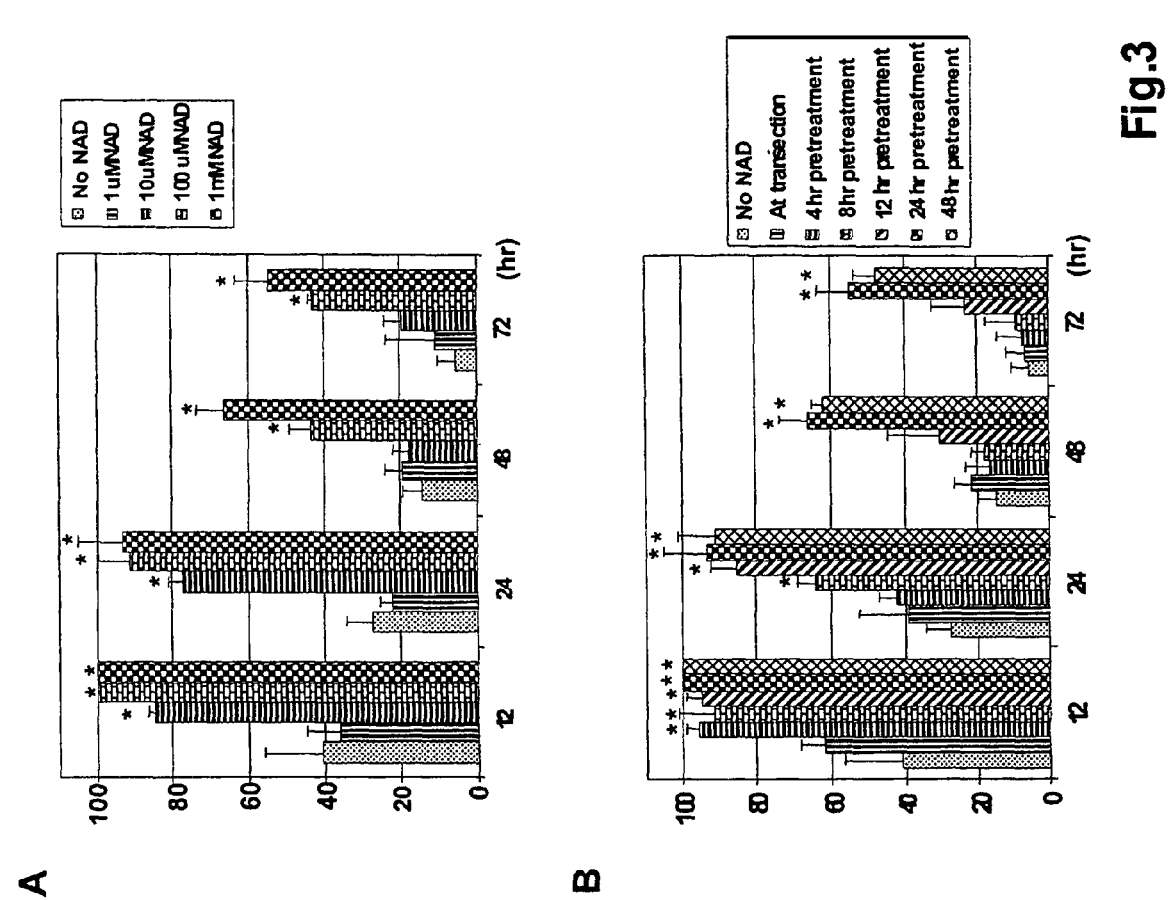
FIG. 3 illustrates that axonal protection requires pre-treatment of neurons with NAD prior to injury showing:
A) in vitro Wallerian degeneration using DRG explants cultured in the presence of various concentrations of NAD added 24 hr prior to axonal transection; and
B) DRG explants preincubated with 1 mM NAD for 4, 8, 12, 24, or 48 h prior to transection wherein the bar chart shows the number of remaining neurites in each experiment (percentage of remaining neurites relative to pre-transection±S.D.) at each of the indicated time points and the "*" indicates significant axonal protection compared to control ($p<0.0001$).

Previous experiments have shown that neuronal cells express membrane proteins that can bind and transport extracellular NAD into the cell (Bruzzone, et al., Faseb J 15:10-12, 2001). This encouraged us to investigate whether exogenously administered NAD could prevent axonal degeneration. We added various concentrations of NAD to neuronal cultures prior to axonal transection and examined the extent of axonal degradation. We found that 0.1-1 mM NAD added 24 hr prior to axotomy significantly delayed axonal degeneration, although exogenously applied NAD was slightly less effective in protecting axons than lentivirus mediated NMNAT1 expression (FIG. 3A). These results provide direct support for the idea that increased NAD supply can prevent axonal degradation.

Example 5

This example illustrates that NAD was required prior to the removal of the neuronal cell bodies to protect the injured neurons from axonal degeneration.

To gain insights into the mechanism of NAD-dependent axonal protection (NDAP), we examined whether NAD was required prior to the removal of the neuronal cell bodies, or whether direct exposure of the severed axons to high levels of NAD was sufficient to provide protection (FIG. 3B). Neuronal cultures were prepared and 1 mM NAD was added to the culture medium at the time of axonal transection or at various times (4 to 48 hr) prior to injury.

We found that administering NAD at the time of axonal transection or, for up to 8 hr prior to injury, had no protective effects on axons. However, significant axon sparing was observed when neurons were incubated with NAD for longer periods of time prior to injury, with the greatest effects occurring after at least 24 h of NAD pre-treatment, These results indicate that NAD dependent axonal protection is not mediated by a rapid post-translational modification within the axons themselves.

The requirement for extended exposure to NAD of the intact neurons to prevent axonal degradation in response to injury suggests that the protective process requires de novo transcriptional and/or translational events. Interestingly, both the Wld$^s$ protein and NMNAT1 are located within the nucleus (data not shown). Similarly, most enzymes that make up the NAD salvage pathway in yeast are also compartmentalized in the nucleus. We compared NAD levels in wild type and NMNAT1 expressing DRG neurons using sensitive microscale enzymatic assays (Szabo, et al., *Proc Natl Acad Sci USA*, 93:1753-58, 1996), however no changes in overall cellular NAD levels were found (data not shown). This is similar to observations in yeast, in which activation of this nuclear pathway did not change overall levels of NAD (Anderson, et al., *J Biol Chem*, 277:18881-90, 2002; Huh, et al., *Nature*, 425:686-91, 2003). Furthermore, levels of tissue NAD in the brains of wild type and wld$^s$ mice are similar despite the increased levels of NMNAT activity in wld$^s$ mice (Mack, et al., *Nat Neurosci*, 4:1199-206, 2001). These data suggest that an NAD-dependent enzymatic activity in the nucleus, as opposed to cytoplasmic NAD-dependent processes, is likely to mediate the axonal protection observed in response to increased NMNAT activity.

Example 6

This example shows that inhibition of Sir2 is involved in NAD-dependent axonal protection.

Figure 4:
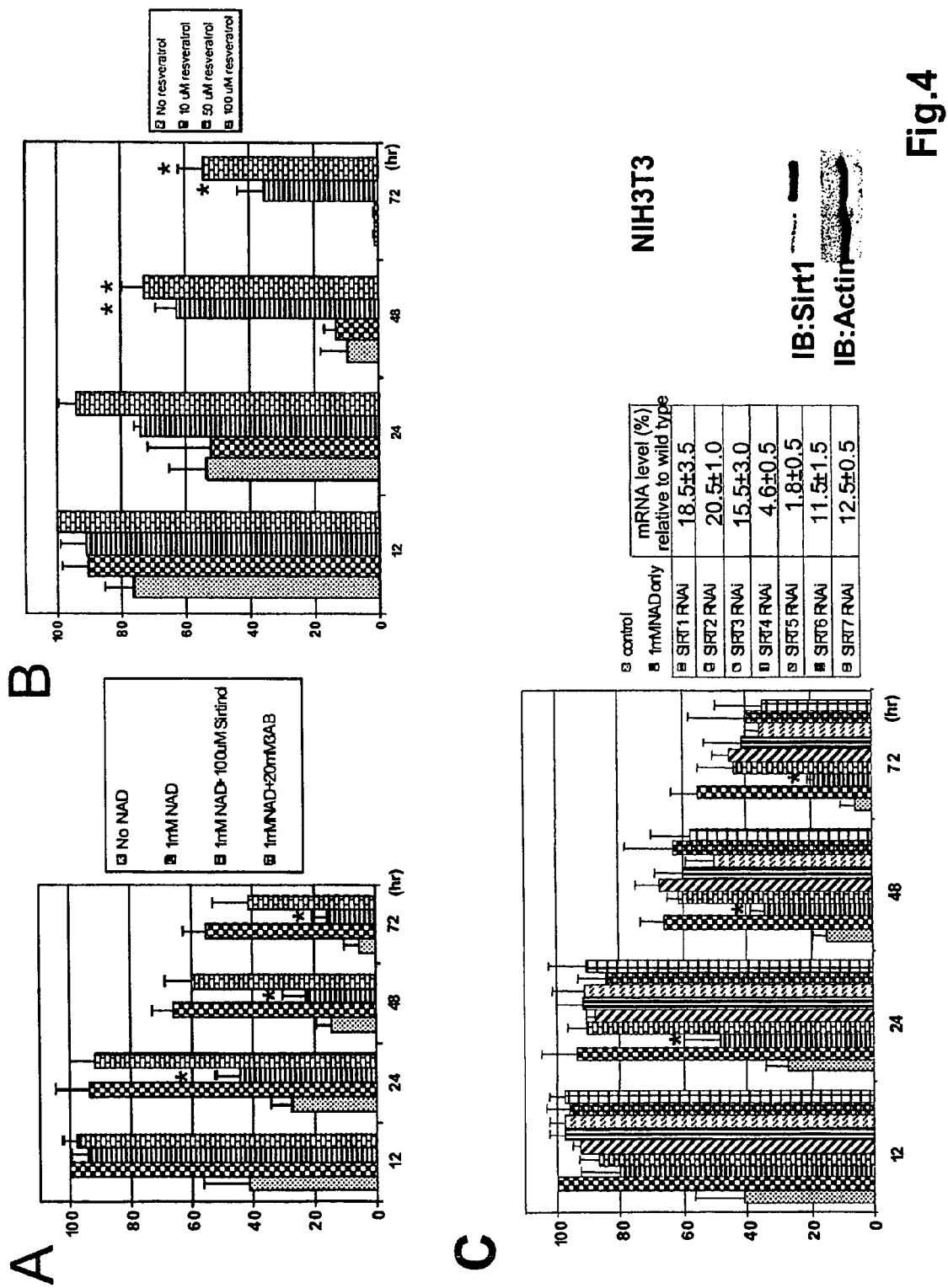
FIG. 4 illustrates that NAD-dependent Axonal Protection is mediated by SIRT1 activation showing.

The Sir2 family of protein deacetylases and poly(ADP-ribose) polymerase (PARP) are the major NAD-dependent nuclear enzymatic activities. Sir2 is an NAD-dependent deacetylase of histones and other proteins, and its activation is central to promoting increased longevity in yeast and *C. elegans* (Bitterman, et al., *Microbiol Mol Biol Rev*, 67:376-99, 2003; Hekimi, et al., *Science* 299:1351-54, 2003). PARP is activated by DNA damage and is involved in DNA repair (S. D. Skaper, *Ann NY Acad Sci,* 993:217-28 and 287-88, 2003). These enzymes, in particular the Sir2 proteins, have generated great interest in recent years as they provide a potential link between caloric restriction and its effects on the ageing process. The importance of these NAD-dependent enzymes in regulating gene activity, prompted us to investigate their role in the self-destructive process of axonal degradation. We therefore tested whether inhibitors of Sir2 (Sirtinol) and PARP (3-aminobenzamide (3AB)) could affect NAD-dependent axonal protection (NDAP) (FIG. 4A). Neurons were cultured in the presence of 1 mM NAD and either Sirtinol (100 μM) or 3AB (20 mM). Axonal transection was performed by removal of the neuronal cell bodies and the extent of axonal degradation was assessed 12 to 72 hr later. We found that Sirtinol effectively blocked NDAP, indicating that Sir2 proteins are likely effectors of this process. In contrast, 3AB had no effect on NDAP, indicating that PARP does not play a role in axonal protection. To further examine the role of Sir2 proteins in NDAP, we tested the effects of resveratrol (10~100 μM), a polyphenol compound that enhances Sir2 activity (Howitz, et al., *Nature,* 425:191-96, 2003). We found that neurons treated with resveratrol prior to axotomy showed a decrease in axonal degradation that was comparable to that obtained using NAD (FIG. 4A), providing further support for the idea that Sir2 proteins are effectors of the axonal protection mediated by increased NMNAT activity.

Example 7

This example shows that SIRT1 is involved in NAD-dependent axonal protection.

In humans and rodents, seven molecules sharing Sir2 conserved domain (sirtuin (SIRT)1 through 7) have been identified, although some of these proteins do not appear to have histone/protein deacetylase activity (Buck, et al., *J Leukoc Biol*, S0741-5400, 2004). SIRT1 is located in the nucleus and is involved in chromatin remodeling and the regulation of transcription factors such as p53 (J. Smith, *Trends Cell Biol*, 12:404-406, 2002). The cellular location of other SIRT proteins is less clear, but some have been found in the cytoplasm and in mitochondria. To determine which SIRT protein(s) is involved in NAD-dependent axonal protection, we performed knockdown experiments using siRNA constructs to specifically target each member of the SIRT family. Neurons were infected with lentiviruses expressing specific SIRT siRNA constructs that effectively suppressed expression of their intended target (FIG. 4B). The infected neurons were cultured in 1 mM NAD and axonal transection was performed by removing the cell bodies. We found that the SIRT1 siRNA construct was just as effective at blocking the axonal protective effects of NAD as the Sirtinol inhibitor. In contrast, inhibition of the other SIRT proteins did not have significant effects on NDAP (FIG. 4B). These results indicate that SIRT1 is the major effector of the increased NAD supply that effectively prevents axonal self destruction. Although, SIRT1 may deacetylate proteins directly involved in axonal stability, its predominantly nuclear location, along with the requirement for NAD ~24 hr prior to injury for effective protection, suggest that SIRT1 regulates a genetic program that leads to axonal protection.

Axonal degeneration is an active, self-destructive phenomenon observed not only after injury and in response to chemotherapy, but also in association with aging, metabolic diseases such as diabetic neuropathy, and neurodegenerative diseases. Our results indicate that the molecular mechanism of axonal protection in the wld$^s$ mice is due to the increased supply of NAD resulting from enhanced activity of the NAD salvage pathway and consequent activation of the histone/protein deacetylase SIRT1.

Examples 8-11

The following Materials and Methods were used in Examples 8-11.

Construction of expression plasmids and mutagenesis. Coding regions of the NAD biosynthetic enzymes were PCR amplified from EST clones BC038133 for murine NMNAT1 and BC005737 for murine nicotinamide mononucleotide adenylyltransferase3 (NMNAT3), using Herculase (Stratagene). Human NAD synthetase (QNS) hexahistidine-tagged cDNA was kindly provided by Dr. N. Hara (Shimane University, Shimane, Japan). Hexahistidine tag was added at the 3'-end of each cDNA. NMNAT1 cytosolic mutant (cytNMNAT1) was generated by PCR-mediated site-directed mutagenesis. Nuclear form of NMNAT3 (nucNMNAT3) was generated by adding a nuclear localization signal to the C-terminal end of NMNAT3. Each PCR amplified NAD synthetic enzyme fragment was cloned into FCIV lentiviral shuttle vector as previously described. The integrity of all the constructs was sequenced using Taq DyeDeoxy Terminator cycle sequencing kits (Applied Biosystems) and an Applied Biosystems 373 DNA sequencer.

NAD biosynthetic substrates. All substrates for NAD biosynthetic enzymes were purchased from Sigma (Na, Nam, NMN, NaMN, nicotininc acid adenine dinucleotide (NaAD), and NAD). NmR was synthesized from NMN. Conversion of NMN to NmR was confirmed by HPLC (Waters) using reverse phase column LC-18T (Supelco). NmR is eluted 260±10 seconds and NMN is eluted 150±10 seconds under 1 ml/min flow rate of buffer containing 50 mM $K_2HPO_4$ and 50 mM $KH_2PO_4$ (pH 7.0). Biological activity of NmR was accessed as previously described by using yeast strains kindly provided from Dr. Charles Brenner (Dartmouth Medical School, N.H., USA).

Real-time quantitative reverse transcription-PCR analysis. All the surgical procedures were performed according to National Institute of Health guidelines for care and use of laboratory animals at Washington University. For the expression analysis following nerve injury, the sciatic nerves of a C57BL/6 mouse was transected and L4 to L5. DRGs were collected at indicated time points and pooled to extract RNA. Rat DRG explants from E14.5 embryo were cultured for 14 days according to the method described and cultured with media containing 10 nM vincristin for indicated period and extracted RNA. Total RNAs from pooled tissue sources or DRG explant cultures were prepared. First-strand cDNA templates were prepared from 1 μg of each RNA using standard methods. Two independent cDNA syntheses were performed for each RNA sample. Quantitative reverse transcription (RT)-PCR was performed by monitoring in real-time the increase in fluorescence of the SYBR-GREEN dye on a Taq-Man 7700 Sequence Detection System (Applied Biosystems).

Cell culture, in vitro axotomy, and quantification of axonal degeneration. Mouse DRG explants from E12.5 embryos were cultured in the DMEM containing 10% FCS and 1 nM nerve growth factor. Non-neuronal cells were removed from the cultures by adding 5-fluorouracil to the culture media. Transection of neurites was performed at 14-21 DIV using an 18-gauge needle to remove the neuronal cell bodies. Lentiviral expression vectors were generated. Lentiviral infection was performed 3-7 days prior to axonal transection for 24 hr. Quantitative analysis of neurite degeneration was performed.

Determination of protein expression and localization. For confirmation of protein expression, HEK293T cells were infected with a virus that expresses each of NAD biosynthetic enzymes. Cells were lysed 5 days after infection to be analyzed by immunoblot to detect expression of each protein with a hexa-histidine tag by anti-6×His tag monoclonal antibody (R&D Systems). Subcellular localization of each protein was analyzed using HEK293T cells transiently transfected with a viral shuttle vector for each NAD biosynthetic enzymes. Cells were fixed in 4% paraformaldehyde in PBS containing 0.1% tween-20 (PBS-T) and incubated with PBS-T containing 5% BSA for 1 hour, and then covered with 1:1000 diluted anti-6×His tag antibody (R&D Systems) in PBS-T containing 1% BSA and for 16 hours at 4° C. Cells were washed with PBS-T and incubated with Alexa Fluor 594-conjugated secondary antibody (Molecular Probes) in TBS-T for 1 hour and examined by fluorescence microscopy (Nikon).

NMNAT protein overexpression, affinity purification and enzymatic assay. HEK293T cells were transfected with an expression plasmid for each enzyme by using calcium phosphate precipitation. Three days later, cells were washed with PBS twice and then suspended in the buffer containing 50 mM Sodium Phosphate (pH8.0), and 300 mM NaCl (buffer A). Cells were then homogenized by SONIFIRE 450 (BRANSON) and supernatant was collected by centrifugation at 10,000 g for 10 min. His-select Nickel Affinity Gel (Sigma) was washed with buffer A and 0.1 ml of 50% gel suspension was added to 1 ml of supernatant and incubated for 10 min at 4° C., then beads binding hexa-histidine-tagged protein was extensively washed with the buffer A. Proteins were eluted by adding 100 μl of the solution containing 50 mM Sodium Phosphate (pH 8.0), 300 mM NaCl, and 250 mM imidazole. Relative NMNAT enzymatic activity was measured by using affinity purified proteins as described before and subtracted the value obtained from mock transfected cells and normalized by the amount of recombinant protein determined by densitometry.

Administration of NAD biosynthetic substrates and optic Nerve transection. Nam, NMN, NmR, or NAD was dissolved in PBS at the concentration of 100 mM or 1 M. Each of 5 μl solution was injected into left intravitreal component under the anesthesia at a rate of 0.5 μl ml per second. The left optic nerve was transected at 24 hours after intravitreal injection and optic nerve was recovered at indicated time. Optic nerve tissue was homogenized in 100 μL of a buffer containing 100 mM tris-HCl (pH 6.8), 1% SDS, and 1 mM DTT. Fifty μg of protein for each sample was analyzed by the Western blotting using anti-neurofilament antibody 2H3 (Developmental Studies Hybridoma Center) and peroxidase-conjugated secondary antibody (Jackson ImmunoResearch). The degeneration rate was calculated from the ratio of the neurofilament immunoreactivity of transected vs. contralateral nerves.

Example 8

This example illustrates the NAD biosynthetic pathway and expression analysis of mammalian NAD biosynthetic enzymes.

NAD is synthesized via three major pathways in both prokaryotes and eukaryotes. In the de novo pathway, NAD is synthesized from tryptophan (FIG. 5). In the salvage pathway, NAD is generated from vitamins including nicotinic acid and nicotinamide. A third route from nicotinamide riboside called Preiss-Handler independent pathway has recently been discovered. The last enzymatic reaction of the de novo pathway involves the conversion of quinolinate to NaMN by QPRT (EC 2.4.2.19). At this point, the de novo pathway converges with the salvage pathway. NaPRT (EC 2.4.2.11) converts Na to NaMN, which is then converted to NaAD by NMNAT (EC 2.7.7.1). QNS1 (EC 6.3.5.1) converts NaAD to NAD. NmPRT (EC 2.4.2.12); also reported as visfatin) converts Nam to NMN. NMN is also converted to NAD by NMNAT. Nicotinamidase (PNC, EC 3.5.1.19), which converts Nam to Na in yeast and bacteria salvage pathway has not been identified in mammals. In the Preiss-Handler independent pathway, Nrk (EC 2.7.1.22) converts NmR to NMN and converge to salvage pathway. Most of these mammalian enzymes including QPRT, NMPRT, QNS1, Nrk1/2 and NMNAT1/2/3 have previously cloned and characterized. A mammalian homologue of NaPRT was also identified as an EST annotated as a mammalian homolog of a bacterial NaPRT.

To investigate the expression of mammalian NAD biosynthetic enzymes in the nervous system, we performed quantitative RT-PCR using RNA from mouse brain, retina, spinal code, and DRG at age of E14, P0, P7, P14 and P21. All enzymes are expressed ubiquitously in the nervous system throughout the development and in adulthood, with an exception of Nrk2, whose expression is very low in all examined tissues (data not shown). To identify inducibility of NAD-synthesizing enzymes in response to neuronal insults, we compared the RNA expression of each enzyme in DRGs at 1, 3, 7, and 14 days after sciatic nerve transection against non-injured DRG. As shown in FIG. 6A, most of the enzymes were up-regulated 2 to 8-fold after injury. Among those, Nrk2 expression is exceptionally highly induced (more than 20-fold) at 14 days after axotomy. We also analyzed expression of NAD synthetic enzymes during the axonal degeneration caused by neurotoxin in cultured rat DRG neuron. DRG neurons were treated with 0.1 μM and 1 μM rotenone to cause axonal degeneration and collected RNA at 24 hours after the addition of rotenone. The expression of Nrk2 was increased more than 6 folds after rotenone treatment (FIG. 6B). These results suggest that, while all enzymatic activities in NAD synthesis pathway is ubiquitously present, Nrk2 may be responsible for supplying NAD synthesizing substrate after neuronal insults.

Example 9

This example illustrates that both nuclear and cytoplasmic Nmat enzymes save axons from degeneration.

To determine whether nuclear localization of NMNAT1 is essential to provide the axonal protection, we analyzed the effect of subcellular distribution of NMNAT enzyme in the in vitro Wallerian degeneration assay and compared the extent of axonal protection between overexpression of cytoplasmic and nuclear NMNAT. NMNAT1 has putative nuclear localization signal PGRKRKW in the 211-217 amino-acids of NMNAT1 protein. We generated a mutant NMNAT1 designated as cytNMNAT1 in which this nuclear localization signal was altered as PGAAAAW and examined subcellular distribution. As shown in FIG. 7B, the majority of cytNMNAT1 located in the cytosol as we expected.

Next we confirmed enzymatic activity of cytNMNAT1, NMNAT1 and its mutant cytNMNAT1 were purified from the cell lysate expressing either of proteins by using affinity gel. The enzymatic activity of affinity purified proteins was measured as described above and we found that cytNMNAT1 activity did not altered by its mutation (FIG. 7C). After the overexpression of cytNMNAT1 in DRG neurons, we observed strong neurite protection as well as nuclear wild NMNAT1 (FIGS. 7A, E). We further confirmed this result by using NMNAT1 isoenzyme that lacks nuclear localization signal. Among two NMNAT isoenzymes, NMNAT3 is previously reported to locate outside nucleus and mitochondria, and have comparable enzymatic activity to NMNAT1. We added nuclear localization signal KPKKIKTED of human topoisomerase I to the C-terminal of NMNAT3 to generate nuclear NMNAT3. We expressed hexa-histidine tagged NMNAT3 or nucNMNAT3 in HEK293T cells and analyzed subcellular localization and its enzymatic activity. NMNAT3 was distributed outside the nucleus including bright punctuate staining as reported before and nucNMNAT3 mainly localized in the nucleus with some punctuate staining in the cytosol (FIG. 7B). The enzymatic activity of NMNAT3 and nucNMNAT3 were measured and both proteins have comparable enzymatic activity compared with NMNAT1 (FIG. 7C). Then, in vitro Wallerian degeneration assay was performed after overexpression of these two NMNAT3 enzymes, and we found that overexpression of both NMNAT3 and nucNM-NAT3 showed same extent of delay in neurite degeneration as well as NMNAT1 (FIGS. 7A, E). The lentivirus mediated expression of each enzyme was confirmed by Western blotting (FIG. 7D). These experiments confirmed that NMNAT targeted to either the nucleus or cytosol protects neurite from degeneration.

Example 10

This example illustrates that exogenous application of substrates for NAD biosynthetic enzymes protects axon from degeneration.

We have previously shown that exogenously applied NAD in the culture medium shows axonal saving effect in vitro. Here we showed that expression of NmPRT also shows axonal protection suggesting that Nam is used as a substrate for NAD synthesis in neurons. To determine which substrate shown in FIG. 5 is used for NAD synthesis in neurons and to identify whether any of NAD precursors may be able to save axons similar to or possibly better than NAD, we applied Na, Nam, NmR, NaMN, NMN, or NaAD in the culture media and performed in vitro Wallerian degeneration assay. An application of 1 mM NMN for 24 hours before neurite transection successfully saved neurites from degeneration. Quantitative analysis revealed that NMN treatment results in neurite protection to an extent similar to that achieved by exogenously applied NAD (FIG. 8B). These results further suggested the possibility that increased supply of other NAD biosynthetic substrates have an ability to save neurites from degeneration. We then exogenously applied 1 mM of NAD biosynthetic substrates including Na, Nam, NaMN, NaAD, and NmR to the DRG neurons for 24 hours and performed neurite transection. As shown in FIGS. 8A and B, NaMN or NmR treatment also saved neurites as well as NAD. NaAD showed slight protection but Na failed to save neurites, while Na and Nam had no effect. Quantitative analysis revealed that exogenous application of 1 mM NaMN, NMN, NmR, or NAD caused comparable increase in intact neurites at 48 hours after transection (FIG. 8B). Because the protective effect of NaMN is equal to NMN, a step synthesize NAD from NaAD by QNS is active enough to save neurites under the increased supply of NaAD. Nevertheless, exogenous application of NaAD shows less increase in intact neurites at 48 hours compared with NAD (FIG. 8B). This indicates insufficient incorporation into the cell or instability of NaAD in our assay condition. These experiments suggest that there are several different ways to save neurites including exogenous application of NMN, NaMN, and NmR. All of these treatments seem to cause increased supply of NAD and it is consistent to the previous experiments showing NAD application or NMNAT1 overexpression save neurites from degeneration.

Example 11

This example demonstrates that intraviteal application of NAD biosynthetic substrates delays the axonal degeneration of retinal ganglion cells.

Transection of optic nerve is an in vivo model which can be used to investigate mechanisms leading to Wallerian degeneration and following retinal ganglion cell (RGC) death observed in human diseases such as glaucoma. In the C57BL/Wlds mouse strain, optic nerve degeneration during Wallerian degeneration after axotomy is dramatically slowed. In addition, intravitreal injection is used for screening of compounds that protect RGC axon from degeneration in vivo and thus we can asses the axon protective effect of each NAD biosynthetic substrates in vivo by intraocular injection of compounds including NAD, NMN, NmR, and Nam. From in vitro Wallerian degeneration assay, 1 mM of NAD, NMN, and NmR in the culture media is enough to protect axon from degeneration. We initially injected 5 μl of 100 mM or 1 M NAD solution into left intravitreal compartment. After 24 hours incubation, left optic nerve was transected and control (right) and axotomized (left) optic nerve were collected at 3, 4, and 5 days after transection. Neurofilament immunoreactivity from the axotomized optic nerve was measured and normalized against the value obtained from the right side of the optic nerve. We found that the immunoreactivity at 4 days after transection was 77±27% and 78±22% of non-axotomized optic nerve in 1 M and 100 mM NAD injected rats respectively, while control animal showed only 7±16% (FIG. 9)

We then injected 5 μl of 100 mM NMN, NmR, and Nam into left intravitreal compartment and collected optic nerves at 4 days after left optic nerve transaction. The immunoreactivity obtained from NMN and NmR injected optic nerve was 60±25 and 72±19% of non-axotomized nerve. Nam injected animals did not show any difference from the control animals. These results are consistent with the in vitro study that showed NAD, NMN, and NmR have axon saving activity but Nam does not. Our in vivo study revealed that these small molecules that are involved in the NAD biosynthetic pathway are useful tools to save axon from degeneration.

All references cited in this specification are hereby incorporated by reference. Any discussion of references cited herein is intended merely to summarize the assertions made by their authors and no admission is made that any reference or portion thereof constitutes relevant prior art. Applicants reserve the right to challenge the accuracy and pertinency of the cited references.

What is claimed is:

1. A method of treating an axonopathy in a mammal in need thereof, the method comprising administering to the mammal an agent that acts by increasing sirtuin activity in diseased and/or injured neurons and supporting cells in an amount effective to decrease axonal degeneration.

2. A method according to claim 1, wherein the agent acts by increasing SIRT1 activity.

3. A method according to claim 1, wherein the agent is NAD, NADH, an intermediate of a de novo pathway for synthesizing NAD, an intermediate of a NAD salvage pathway, an intermediate of a nicotinamide riboside kinase pathway or a combination thereof.

4. A method according to claim 1, wherein the agent is NAD, nicotinamide mononucleotide, nicotinic acid mononucleotide or nicotinamide riboside.

5. A method according to claim 1, wherein the mammal is a human.

6. A method in accordance with claim 4 wherein the agent is nicotinamide riboside.

* * * * *